(12) United States Patent
Zheng et al.

(10) Patent No.: US 7,220,842 B2
(45) Date of Patent: May 22, 2007

(54) IMMUNOASSAYS FOR BUPRENORPHINE AND NORBUPRENORPHINE

(75) Inventors: Yi-Feng Zheng, Wilmington, DE (US); Pratap Singh, Wilmington, DE (US); Dorota Bolle, Newark, DE (US); Hshiou-Ting Liu, Miltipas, CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 10/818,115

(22) Filed: Apr. 5, 2004

(65) Prior Publication Data

US 2005/0221405 A1 Oct. 6, 2005

(51) Int. Cl.
*C07K 17/02* (2006.01)
*C07D 491/02* (2006.01)
*G01N 33/535* (2006.01)

(52) U.S. Cl. .................. 530/405; 546/46; 435/7.9; 435/188; 530/388.9; 530/389.8; 530/406

(58) Field of Classification Search ................ 435/7.9, 435/188; 530/388.9, 405, 389.8, 406; 546/46
See application file for complete search history.

(56) References Cited

U.S. PATENT DOCUMENTS

| | | | | |
|---|---|---|---|---|
| 5,037,645 | A | 8/1991 | Strahilevitz | 424/85.8 |
| 5,840,712 | A * | 11/1998 | Morgan et al. | 514/52 |
| 5,849,915 | A | 12/1998 | Kim et al. | 546/39 |
| 6,054,127 | A | 4/2000 | Swain et al. | 424/194.1 |
| 6,231,886 | B1 | 5/2001 | Reder et al. | 424/449 |
| 6,344,212 | B2 | 2/2002 | Reder et al. | 424/449 |
| 6,383,490 | B1 | 5/2002 | Wirschling et al. | 424/193.1 |
| 6,518,031 | B2 | 2/2003 | Ennifar et al. | 435/7.1 |
| 2004/0248222 | A1 * | 12/2004 | Root et al. | 435/7.92 |

FOREIGN PATENT DOCUMENTS

EP 314127 * 5/1989

OTHER PUBLICATIONS

C.W. Hand et al, Ann. Clin. Biochem. (1986), vol. 23, pp. 47-53.*
G.K.L. Tiong et al, Naunyn-Schiedeberg's Arch. Pharmacol. (1988), vol. 338, pp. 202-206.*
A.J. Bartlett et al, Eur. J. Clin. Pharmacol. (1980), vol. 18, pp. 339-345.*
Cirimele et al; Enzyme Immunoassay Validation for the Detection of Buprenorphine in Urine, Journal of Analytical Toxicology, vol. 27, Mar. 2003, pp. 103-105.
Kronstrand et al; Analysis of Buprenorphine, Norbuprenorphine and Their Glucuronides in Urine by Liquid Chromatography-Mass Spectrometry, Journal of Analytical Toxicology, vol. 27, Oct. 2003, pp. 464-470.

* cited by examiner

*Primary Examiner*—Mary E. Ceperley
(74) *Attorney, Agent, or Firm*—Leland K. Jordan; Cynthia G. Tymeson

(57) ABSTRACT

Methods, compositions and kits are disclosed directed at haptens, immunogens and immunoassays for buprenorphine (BUP) and nor buprenorphine (norBUP). The method comprises providing in combination in a medium (i) a sample suspected of containing buprenorphine (BUP) or norbuprenorphine (norBUP) and (ii) an antibody raised against an immunogen of buprenorphine (BUP) or norbuprenorphine (norBUP). The medium is examined for the presence of a complex comprising a labeled hapten of buprenorphine (BUP) or norbuprenorphine (norBUP) where the presence of such as complex indicates the presence of the compound in the sample.

28 Claims, 14 Drawing Sheets

(1) Buprenorphine (2) Norbuprenorphine (1b) Buprenorphine-3-β-D-glucuronide (2b) Norbuprenorphine-3-β-D-glucuronide 1) Ab + Analyte + G6PDH-norBUP-Conjugate ⟶ Ab-Analyte
+
G6PDH-norBUP-conjugate-AB
(Inactive)
+
G6PDH-norBUP-conjugate
(Active)

2) Glucose-6-phosphate + $NAD^+$ ⟶ 6-phosphogluconolactone + NADH
(Absorbs at 340 nm)

The rate of increasing absorbance at 340 nm due to the increase of NADH is related to the concentration of analyte in the sample by a mathematical function.

Emit®: Enzyme-multiplied immunoassay technique

Ab: Anti-buprenorphine Anbtibody

Analyte: Buprenorphine, norbuprenorphine

G6PDH: Glucose-6-phosphate dehydrogenase $NAD^+$: Nicotinamide adenine dinucleotide (oxidized form)

NADH: Nicotinamide adenine dinucleotide (reduced form, absorbs at 340 nm)

IMMUNOASSAYS FOR BUPRENORPHINE AND NORBUPRENORPHINE

FIELD OF THE INVENTION

This invention relates to methods, compositions and kits for detecting the presence and/or amounts of entactogens in samples suspected of containing the same. In particular, this present invention relates to homogeneous immunoassays and compositions of matter that are useful in conducting immunoassays for buprenorphine and norbuprenorphine. Homogeneous immunoassays have the advantage of not requiring separation steps. Such assays, however, are limited by the difficulty of providing antibodies which will modulate the activity of a label that is normally bound to the antibodies or an analog of the analyte. The present invention overcomes these difficulties and provides immunoassays for buprenorphine and norbuprenorphine employing glucose-6-phosphate dehydrogenase (G6PDH) enzymes as labels.

BACKGROUND OF THE INVENTION

The clinical diagnostic field has seen a broad expansion in recent years, both as to the variety of materials of interest that may be readily and accurately determined, as well as the methods for the determination. Over the last decade, testing for drugs of abuse has become commonplace. This testing is not only for the monitoring of criminal offenders and drug addicts, but employers also use it for the screening of workers. In recent years, immunoassay based on the reaction of an antibody with an antigen has been extensively investigated for this purpose. Some categories of immunoassays include a radioimmunoassay, using a radioactive isotope, an enzyme-based immunoassay (EIA) using an enzyme, and luminescence assays, using fluorescent labels, e.g., fluorescence polarization, and chemiluminescent labels.

The clinically important and potent analgesic buprenorphine, a semi-synthetic narcotic derived from thebaine, has attracted attention as a potential pharmacotherapy for opiate abuse and dependence. At times of shortage of heroin, buprenorphine, BUP hereinafter may be used as the substitute drug of choice. BUP's unique effects and pharmacology make it an attractive and clinically helpful treatment option. The unique pharmacology of buprenorphine at the mu-opioid receptor (i.e. high affinity, low intrinsic activity and slow dissociation) results in buprenorphine having: (1) a good safety profile, (2) low physical dependence, and (3) flexibility in dose scheduling. Further, BUP produces less euphoria than morphine and heroin. When compared with other opiates, it also causes a significantly lower degree of sedation and respiratory depression, the slowing down of breathing that makes heroin overdoses so dangerous.

On the other hand, BUP has been chosen by the National Institute on Drug Abuse as one of the medications for the treatment of opiate dependence. Norbuprenorphine, norBUP hereinafter, is a major dealkylated metabolite of BUP and displays similar but distinct properties. These limited side effects can be attributed to the fact that BUP and norBUP are partial mu agonists. Agonists are chemicals that bind to and stimulate opiate receptors. Antagonists block the effects of opiates by binding to receptors without stimulating them. By stimulating mu opiate receptors in the brain, mu agonists produce the effects associated with morphine: analgesia, euphoria, sedation, and respiratory depression. Because BUP is a partial mu agonist, it also readily binds to mu opiate receptors. However, BUP activates these receptors to a lesser degree than full mu receptor agonists such as morphine and heroin. Both norBUP and BUP are potent partial agonists, with norBUP having moderate efficacy and BUP having low efficacy. BUP also is released slowly from the mu receptor, producing a long-lasting effect. Therefore, it may be possible to give BUP to patients every other day, rather than in the daily doses that methadone patients must receive. Some studies also suggest that withdrawal effects are less severe with BUP than with methadone. From both a drug of abuse and therapeutic drug monitoring view point, it is important to have available reliable immunoassays for BUP and its metabolite, norBUP. HPLC-MS methods for the detection of buprenorphine and norbuprenorphine are disclosed in the literature [Kronstrand, R.; Selden G.; Josefsson, M. "Analysis of buprenorphine, norbuprenorphine, and their glucuronides in urine by liquid chromatography-mass spectrometry", J. Anal. Toxicol., 2003, 27, (7), p464–70.], and two immunoassays have also been disclosed [Cirimele, V.; Kintz, P.; Lohner, S; Ludes, B. "Enzyme immunoassay validation for the detection of buprenorphine in urine", J. Anal. Toxicol., 2003, 27, (2), p103–5, and Tiong, G. K. L.; Olley, J. E. "Enzyme immunoassay of buprenorphine", Naunyn-Schmiedeberg's Arch Pharmacol 1988, 338, 202] However, these assays are not suitable for use in automated clinical analyzers. There is, therefore, a need for assays for the detection of the aforementioned drugs and, in some instances, their major metabolites. The assays should be able to detect these drugs in order to monitor and treat addicted patients.

SUMMARY OF THE INVENTION

The present invention relates to methods for immunoassay of the analytes BUP and norBUP. In particular, the invention relates to the use of derivatives of BUP and norBUP in a signal producing system. The invention also relates to the use of immunogens of BUP and norBUP to be used in producing antibodies for capture of such analytes.

The present invention specifically provides the syntheses of buprenorphine and norbuprenorphine haptens, immunogens and bio-conjugates by placing a linker on the hydroxyl functional group at the benzene ring of buprenorphine and norbuprenorphine molecules and coupling through the linker to a protein or the label enzyme. The present invention further provides the syntheses of norbuprenorphine immunogens and bio-conjugates starting from norbuprenorphine and coupling through the nitrogen atom of norbuprenorphine molecule with a linker to a protein or the label enzyme. The present invention even further provides the syntheses of buprenorphine and norbuprenorphine haptens, immunogens and bio-conjugates by placing a linker on the oxygen atom of the methoxy group or the hydroxyl group on the t-butyl functionality and coupling through the linker to a protein or label enzyme.

An exemplary embodiment of the present invention is a compound of Formula 1 shown below:

Formula 1

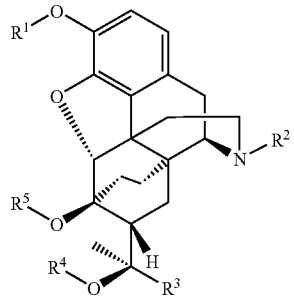

wherein $R^1$ is —Y-Z, and Y is a linking group and Z is selected from the group consisting of hydrogen, —OH, —SH, —S-acyl; —O-lower alkyl, halogen, NH2, -epoxy, -maleimidyl, haloacetamide, carboxyl and all its activated forms including hydroxysuccinimidyl,-succinimidyl,-carbonate, anhydride and imidate, an immunogenic carrier, a protein or a label, and including acid salts thereof;

$R^2$ is a cyclopropyl methyl group;

$R^3$ is a t-butyl group, or lower alkyl group;

$R^4$ is hydrogen, or lower alkyl group; and, $R^5$ is a methyl group or lower alkyl group.

Another exemplary embodiment of the present invention is a compound of Formula 2 shown below:

Formula 2

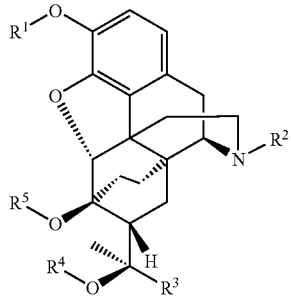

wherein $R^1$ is —Y-Z, and Y is a linking group and Z is selected from the group consisting of hydrogen, —OH, —SH, —S-acyl; —O-lower alkyl, halogen, NH2, -epoxy, -maleimidyl, haloacetamide, carboxyl and all its activated forms including hydroxysuccinimidyl,-succinimidyl,-carbonate, anhydride and imidate, an immunogenic carrier, a protein or a label, and including acid salts thereof;

$R^2$ is H or a protecting group;

$R^3$ is a t-butyl group, or lower alkyl group;

$R^4$ is hydrogen, or lower alkyl group; and, $R^5$ is a methyl group or lower alkyl group.

Another exemplary embodiment of the present invention is a compound of Formula 3 shown below:

Formula 3

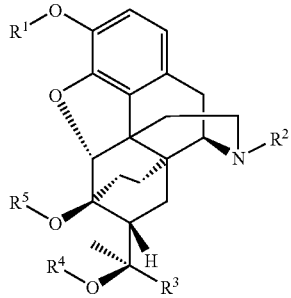

wherein $R^1$ is H, or 3-β-D-glucoronide;

$R^2$ is —Y-Z, and Y is a linking group and Z is selected from the group consisting of hydrogen, —OH, —SH, —S-acyl; —O-lower alkyl, halogen, NH2, -epoxy, -maleimidyl, haloacetamide, carboxyl and all its activated forms including hydroxysuccinimidyl,-succinimidyl,-carbonate, anhydride and imidate, an immunogenic carrier, a protein or a label and including acid salts thereof;

$R^3$ is a t-butyl group, or lower alkyl group;

$R^4$ is hydrogen, or lower alkyl group; and, $R^5$ is a methyl group or lower alkyl group.

Another exemplary embodiment of the present invention is a compound of Formula 4 shown below:

Formula 4

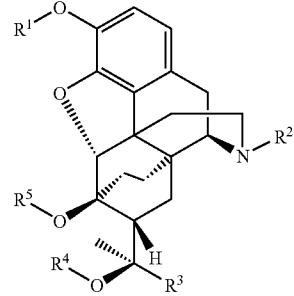

wherein $R^1$ is hydrogen, or protecting group, or 3-β-D-glucoronide;

$R^2$ is a cyclopropyl methyl group, hydrogen or a protecting group;

$R^3$ is a t-butyl group, or lower alkyl group;

$R^4$ is —Y-Z, and Y is a linking group and Z is selected from the group consisting of hydrogen, —OH, —SH, —S-acyl; —O-lower alkyl, halogen, NH2, -epoxy, -maleimidyl, haloacetamide, carboxyl and all its activated forms including hydroxysuccinimidyl,-succinimidyl,-carbonate, anhydride and imidate, an immunogenic carrier, a protein or a label; and, $R^5$ is a methyl group, or lower alkyl group.

Another embodiment of the present invention is a compound of Formula 5 as shown below:

Formula 5

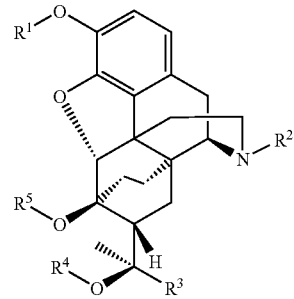

wherein $R^1$ is hydrogen or protecting group or 3-β-D-glucoronide;

$R^2$ is cyclopropyl methyl group, hydrogen or protecting group;

$R^3$ is a t-butyl group, or lower alkyl group;

$R^4$ is a methyl group, or lower alkyl group; and, $R^5$ is —Y-Z, and Y is a linking group and Z is selected from the group consisting of hydrogen, —OH, —SH, —S-acyl; —O-lower alkyl, halogen, NH2, -epoxy, -maleimidyl, haloacetamide, carboxyl and all its activated forms including hydroxysuccinimidyl,-succinimidyl,-carbonate, anhydride and imidate, an immunogenic carrier, a protein or a label, and including acid salts thereof.

Another embodiment of the present invention is a method for determining a compound selected from the group consisting of buprenorphine (BUP), and norbuprenorphine (nor-BUP). The method comprises providing in combination in a medium: (a) a sample suspected of containing the compound; and, (b) an antibody raised against a compound of any of the above formulas 1–5. The medium is examined for the presence a complex comprising the compound and the antibody where the presence of such as complex indicates the presence of the compound in the sample. In one aspect of the above embodiment, the combination further comprises a labeled conjugate of the above compound.

Another embodiment of the present invention is a kit for determining a compound selected from the group consisting of buprenorphine (BUP) and norbuprenorphine (norBUP). The kit comprises (a) an antibody raised against buprenorphine (BUP) and norbuprenorphine (norBUP); (b) ancillary reagents for determining the compound; and, (c) a labeled conjugate of a compound of any of the above formulas 1–5. The antibody of the kit may be an antibody raised against a compound of any of the formulas 1–5 above.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
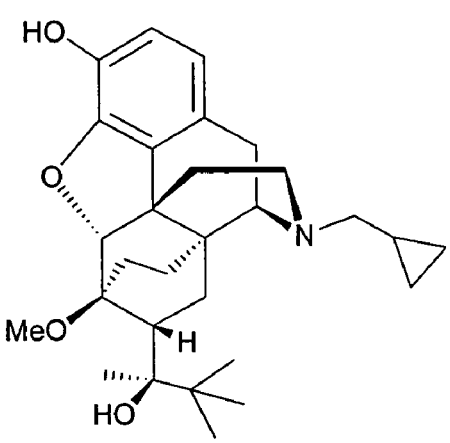
FIG. 1 shows the known chemical structures of buprenorphine and norbuprenorphine and their D-glucuronide conjugates.
Figure 1:
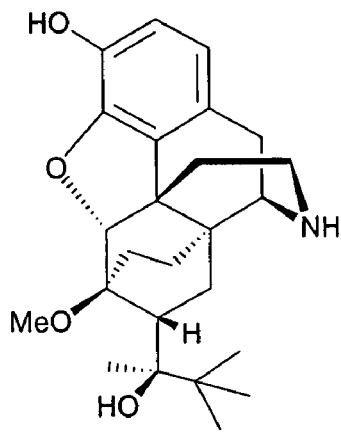
Figure 1:
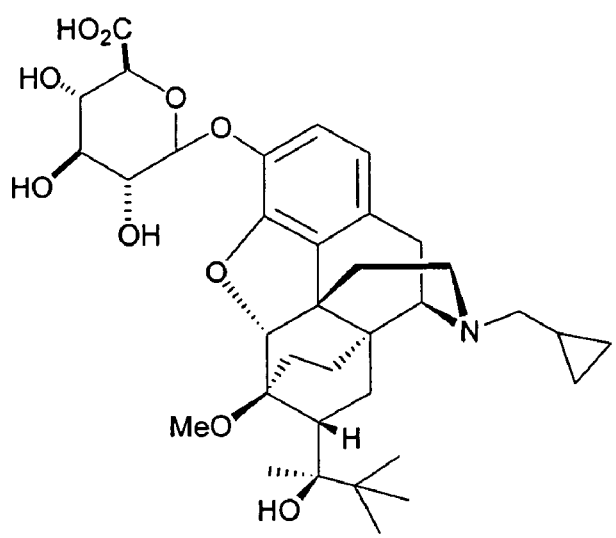
Figure 1:
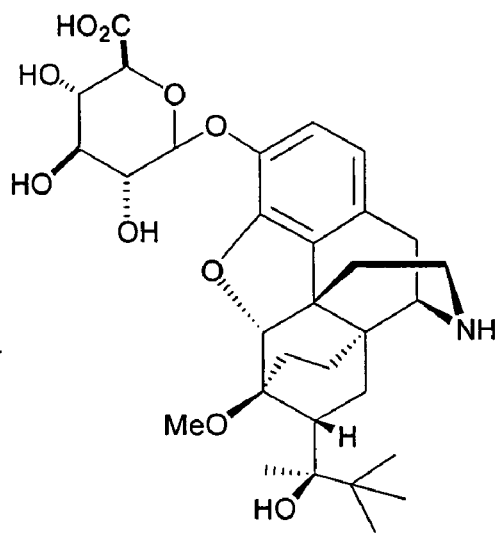

Before proceeding further with the description of the specific embodiments of the invention, a number of terms will be defined.

Definitions

Analyte

The compound or composition to be measured, the material of interest. The analyte is a member of a specific binding pair (sbp) and may be a ligand, which is mono- or polyvalent, usually antigenic or haptenic, and is a single compound or plurality of compounds which share at least one common epitopic or determinant site.

Sample Suspected of Containing Analyte

Any sample which is reasonably suspected of containing analyte can be analyzed by the method of the present invention. Such samples can include human, animal or man-made samples. The sample can be prepared in any convenient medium which does not interfere with the assay. Typically, the sample is an aqueous solution or a natural fluid, preferably, urine, whole blood, serum, plasma, cerebral-spinal fluid, or saliva more preferably, serum.

Measuring the Amount of Analyte

Quantitative, semiquantitative, and qualitative methods as well as all other methods for determining analyte are considered to be methods of measuring the amount of analyte. For example, a method which merely detects the presence or absence of analyte in a sample suspected of containing an analyte is considered to be included within the scope of the present invention.

Synonyms for the phrase "measuring the amount of analyte" which are contemplated within the scope of the present invention include, but are not limited to, detecting, measuring, or determining analyte; detecting, measuring, or determining the presence of analyte; and detecting, or determining the amount of analyte.

Member of a Specific Binding Pair

A member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, or the like. These will usually be members of an immunological pair such as antigen-antibody.

Ligand

Any organic compound for which a receptor naturally exists or can be prepared. For example, in one context of the present invention, the analyte is a ligand and the present invention provides methods for determining the concentration of the analyte which is a ligand.

Receptor

A receptor is any compound or composition capable of recognizing a particular spatial and polar organization of a molecule. These organized areas of a molecule are referred to as epitopic or determinant sites. Illustrative naturally occurring receptors include antibodies and enzymes.

Linking Group

A linking group is a portion of a structure which connects 2 or more substructures. A linking group has at least 1 uninterrupted chain of atoms extending between the substructures. The atoms of a linking group are themselves connected by chemical bonds. The number of atoms in a linking group is determined by counting the atoms other than hydrogen.

Conjugate

A conjugate is a molecule comprised of two or more substructures bound together, optionally through a linking group, to form a single structure. The binding can be made either by a direct connection (e.g. a chemical bond) between the subunits or by use of a linking group. Within the context of the present invention, a conjugate is a G6PDH enzyme or a label protein including alkaline phosphatase, B-galactosidase and horse radish peroxidase or a chemical label such as a fluorescent, luminescent or colorimetric molecule attached to a hapten, sbp member or analyte analog.

Conjugation

Conjugation is any process wherein two subunits are linked together to form a conjugate. The conjugation process can be comprised of any number of steps.

Hapten

Haptens are capable of binding specifically to corresponding antibodies, but usually do not themselves act as immunogens for preparation of the antibodies. Antibodies which recognize a hapten can be prepared against compounds comprised of the hapten linked to an immunogenic carrier.

Signal Producing System

The signal producing system is utilized in assays for analytes and may have one or more components, at least one component being a mutant G6PDH. The signal producing system generates a signal that relates to the presence or amount of analyte in a sample. The signal producing system includes all of the reagents required to produce a measurable signal. For purposes of the present invention, typically, the G6PDH or a label protein including alkaline phosphatase, B-galactosidase and horse radish peroxidase is conjugated to a sbp member analogous to the analyte.

Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like.

The signal producing system provides a signal detectable by external means, normally by measurement of electromagnetic radiation, desirably by visual examination. For the most part, the signal producing system includes a chromophoric substrate and mutant G6PDH enzyme of the invention, where chromophoric substrates are enzymatically converted to dyes which absorb light in the ultraviolet or visible region.

Ancillary Materials

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Sensitivity

Is used in the sense of detection limit, i.e., the smallest amount of an analyte giving a signal that is distinguishable from the signal obtained in the absence of analyte.

Substantial Change in Enzyme Activity

A change in activity of an enzyme sufficient to allow detection of an analyte when the enzyme is used as a label in an assay for the analyte. Typically, the enzyme's activity is reduced 10–100% preferably 20–99%, more preferably 30–95%.

Inhibitory Antibody

An antibody capable of inhibiting the activity of an enzyme or an enzyme-ligand conjugate upon binding an epitope present on the enzyme. Such antibodies are distinguished from anti-ligand antibodies capable of inhibiting the enzyme activity of enzyme-ligand conjugates upon binding to the ligand.

Specific Embodiments

Homogeneous enzyme immunoassays depend on the availability of enzyme-sbp member conjugates whose enzyme activity can be strongly modulated on binding of the sbp partner. The present invention provides enzyme-sbp member conjugates and antibodies for conducting assays that are useful in homogeneous immunoassays.

Immunogens comprising proteins are synthesized and used to prepare antibodies specific for compounds selected from the group consisting of buprenorphine (BUP), and norbuprenorphine (norBUP). The antibodies may be used in methods for detecting the aforementioned drugs in samples suspected of containing the drugs. Label conjugates are prepared and may be employed in the above methods. Effective screening of samples for the presence of one or more entactogens as referred to above may be realized.

The immunogens and label conjugates may involve an analog of BUP or norBUP linked through the nitrogen or through the hydroxyl group of the benzene ring or through the oxygen atom of the methoxy group or the hydroxyl group on the t-butyl functionality, to a protein or a label, respectively. The linking group may comprise about 1 to 15 atoms and may comprise a chain of from 2 to 8 atoms, each independently selected from the group normally consisting of carbon, oxygen, sulfur, nitrogen, halogen and phosphorous. In some embodiments the linking group comprises 1–15 carbon atoms and/or 0–6 heteroatoms and may include glucuronide. Where the linking group provides attachment of a protein to the hydroxyl group of the benzene ring, the linking group usually comprises at least 5 atoms or, when less than 5 atoms, the linking group does not comprise solely carbon atoms or oxygen atoms. Examples of linking groups include [—$(CH_2)_n$—C(O)—, or —$(CH_2)_n$ C(—$SO_2$)=$CH_2$, or C(O)$(CH_2)_n$— or —C(O)$(CH_2)_n$—NHC(O)—, or —C(O)$(CH_2)_n$—NHC(O)$(CH_2)_n$, or —$(CH_2)_n$ $SCH_2$C(O)—, or —$(CH_2)_n$—C(O)NH—$(CH_2)_n$—, or —$(CH_2)_n$—NH—C(O)—$(CH_2)_n$—, or —C(O)—$(CH_2)_n$—], and n is an integer from 1 to 10, and including salts thereof.

The number of heteroatoms in the linking agents will normally range from about 0 to 6, usually from about 1 to 5. The linking agents may be aliphatic or aromatic. When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities will be linked to amine groups, carboxyl groups, active olefins, alkylating agents, e.g., bromoacetyl. Where an amine and carboxylic acid or its nitrogen derivative or phosphoric acid is linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Various linking agents are well known in the art; see, for example, Cautrecasas, *J. Biol. Chem.* (1970) 245:3059.

Buprenorphine and its metabolites are shown in FIG. 1. Norbuprenorphine is the major metabolite which is also used as a key intermediate for the synthesis of haptens and immunogens. Norbuprenorphine can be either purchased from commercial sources [for example, Ultrafine Inc, Manchester, UK] or prepared by chemical synthesis by N-dealkylation of buprenorphine by removing its cyclopropylmethyl moiety.

To develop a specific assay for buprenorphine (BUP and its analog, norbuprenorphine norBUP), this invention focuses on the unique chemical structure of both molecules. That is, two extra six-member rings and one t-butyl alcohol group in both buprenorphine and norbuprenorphine as compared to morphine and heroin are their specificities in term of chemical structures. These specific chemical structures are retained to prepare immunogens and raise antibodies accordingly.

Figure 2:
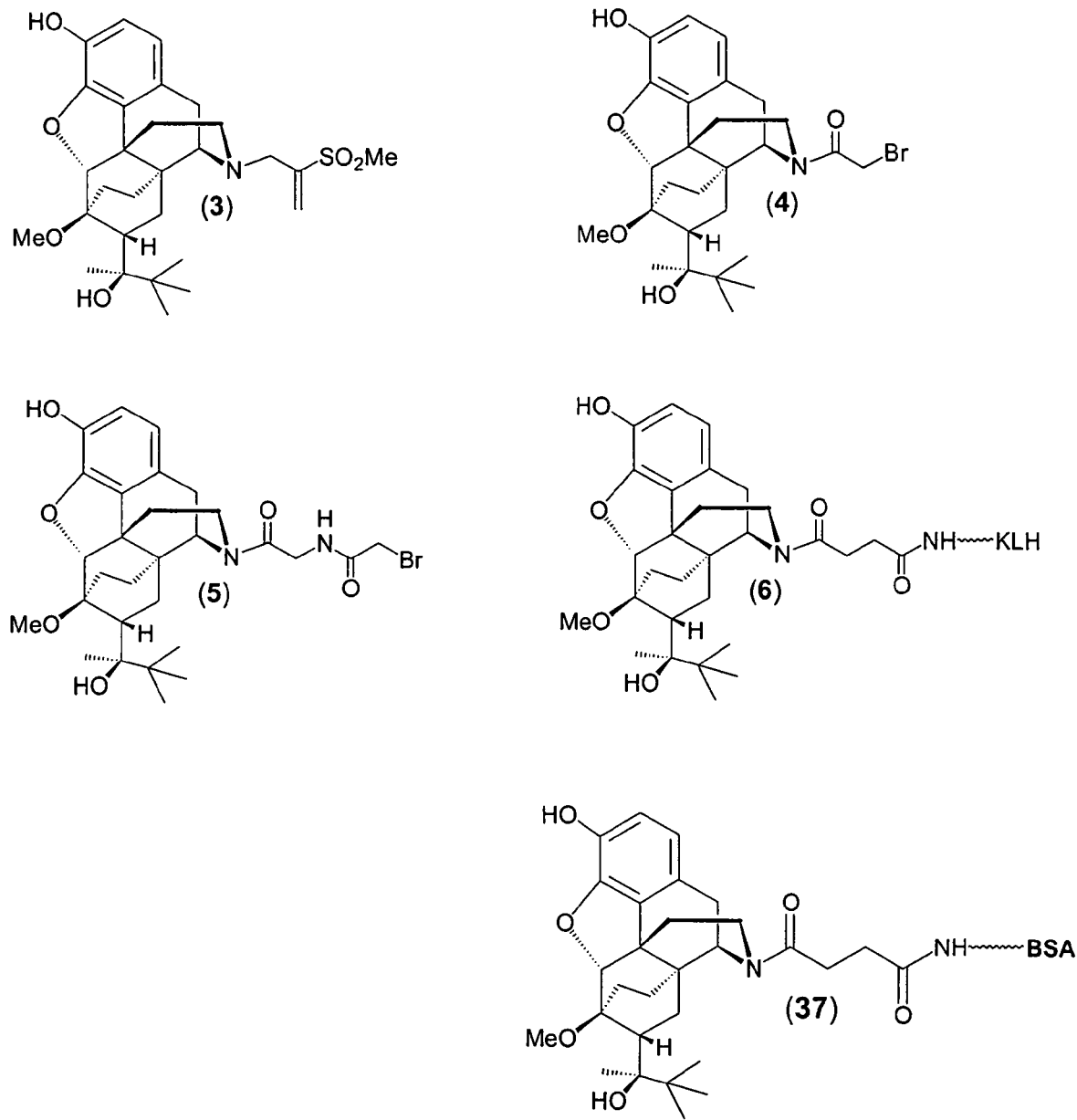
FIG. 2 shows the norbuprenorphine haptens and immunogens by modifying on the nitrogen atom of molecule in the present invention.
Figure 3:
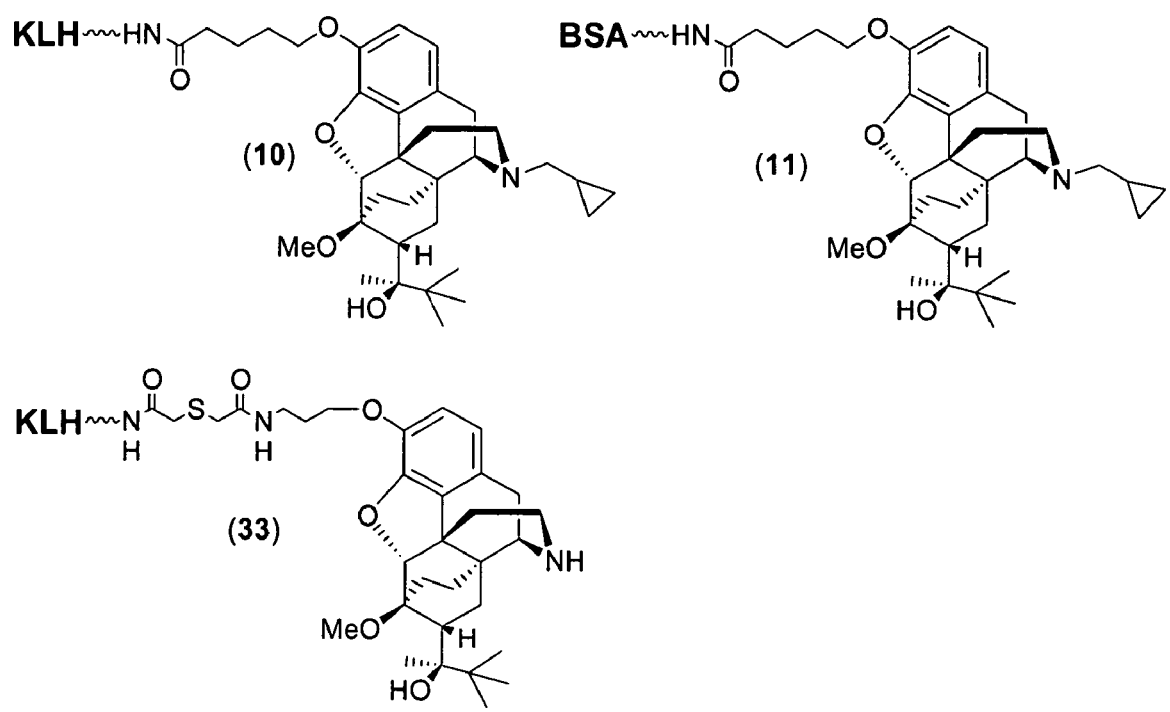
FIG. 3 shows the chemical structures of buprenorphine and norbuprenorphine immunogens by modifying on the benzene ring of molecule in the present invention.
Figure 4:
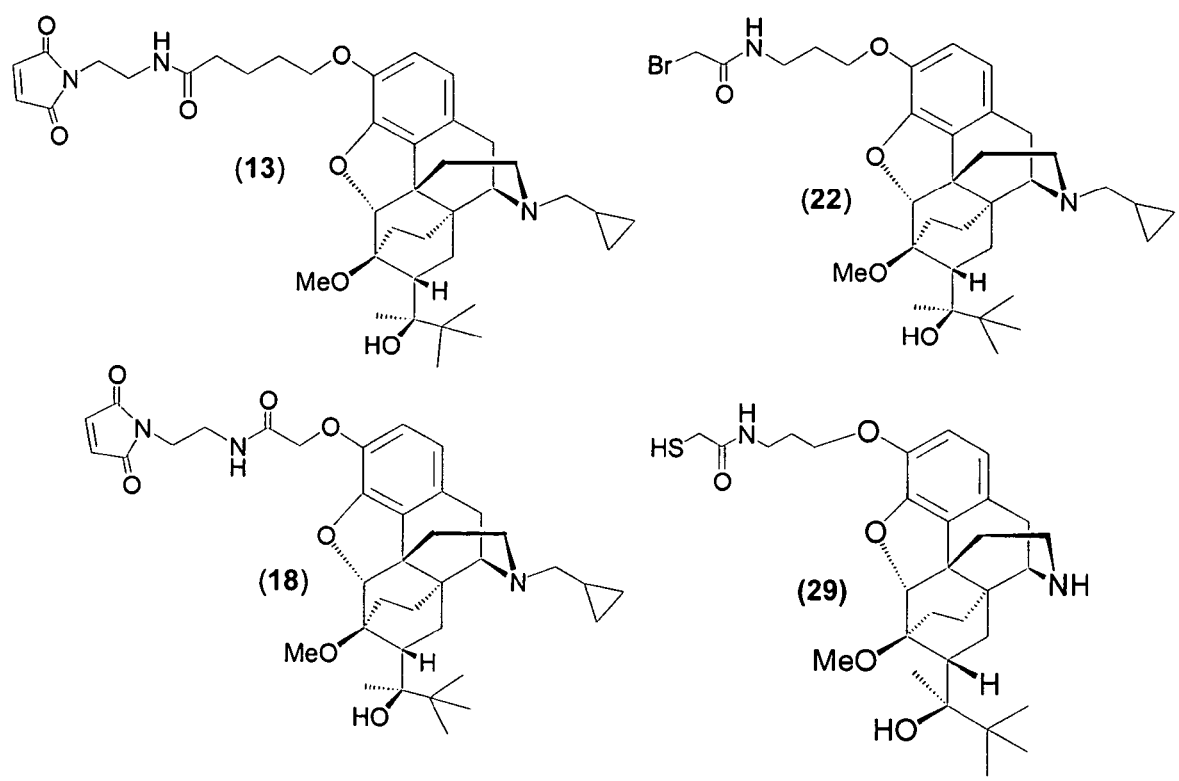
FIG. 4 shows the chemical structures of buprenorphine and norbuprenorphine haptens by modifying on the benzene ring of molecule in the present invention.

The present invention provides for the design of buprenorphine and norbuprenorphine haptens and immunogens by modification of the hydroxyl group on the benzene ring or the amine nitrogen atom or the oxygen atom on the methoxy group or the hydroxyl group on the t-butyl group. Norbuprenorphine haptens (3–5) and immunogens (6) of the present invention are shown in FIG. 2. Placement of a linker (4-atom) to the amine nitrogen of norbuprenorphine provides for antibodies that react with both buprenorphine and norbuprenorphine. Placement of a linker on the hydroxyl group of the benzene ring of buprenorphine and norbuprenorphine for preparation of immunogens (FIG. 3) yields a generation of antibodies which detect both buprenorphine and norbuprenorphine because they share the specificity of the molecular skeleton. However, the derivatives prepared at the OH benzene ringI of either norBUP or BUP as well as derivatives linking through from the oxygen on the methoxy group and the hydroxyl group on the t-butyl group may elicit antibodies that may or may not distinguish buprenorphine from norbuprenorphine. For example, the elicited antibody if generated from a BUP derivative may react only with BUP or may react with BUP and norBUP. Likewise, an antibody elicited from any of the derivatives of norBUP may react only with norBUP or may react with norBUP and BUP. Antibodies that are specific to one or the other of buprenorphine and norbuprenorphine may be utilized for different immunoassay formats. The present invention thusly provides a series of novel buprenorphine and norbuprenorphine derivatives and immunogens useful within various types of immunoassays (FIGS. 2–4).

In addition, linking on the OH of the benzene ring of norBUP or BUP will elicit antibodies that cannot distinguish buprenorphine or norbuprenorphine from each of their gulcuronide metabolites (FIG. 1). Thus, if it is desirable to assay the drug and the gulcuronide metabolite; immunogens may be prepared from this position. Further, such antibodies may or may not distinguish between buprenorphine and norbuprenorphine. Derivatizing at the amine nitrogen cannot elicit antibodies that distinguish between buprenorphine and norbuprenorphine but such antibodies may (or may not) distinguish between their gulcuronide metabolites. In addition, derivatizing at methoxy group and the hydroxyl group on the t-butyl group may distinguish between buprenorphine and norbuprenorphine and the gulcuronide metabolites thereof [1(b) and 2(b) in FIG. 1]. In addition, immunogens prepared from the D-gulcuronide derivatives (or at any OH position on that group) may be used to elicit antibodies to the metabolites and such antibodies may also recognize the parent drug. The present invention thusly provides a series of novel buprenorphine and norbuprenorphine derivatives and immunogens useful within various types of immunoassays (FIGS. 3–4).

Kits

Another aspect of the present invention relates to kits useful for conveniently performing an assay for the determination of an entactogen analyte such as, for example, buprenorphine (BUP) and its analog, norbuprenorphine (norBUP). The kit comprises (a) an antibody raised against buprenorphine (BUP) or norbuprenorphine (norBUP); (b) ancillary reagents for determining the compound; and, (c) a labeled conjugate of a compound of any of the above formulas 1–5. The antibody of the kit may be an antibody raised against a compound of any of the formulas 1–5.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The description below of certain exemplary embodiments of kits uses the language "and/or," which means that the kit may or may not contain each item mentioned. This language is used for the sake of brevity. In general, an immunoassay kit will include at least one antibody for an immunogen of an analyte, e.g., buprenorphine (BUP), and at least one enzyme conjugate that corresponds to that analyte, e.g., an enzyme conjugate of a derivative of buprenorphine (BUP).

A particular embodiment of the present invention is a kit for an assay for the analyte buprenorphine (BUP) comprising in packaged combination:
(i) an antibody raised against the compound of any of the above formulas 1–5; and,
(ii) a conjugate of a derivative of the analyte.

A particular embodiment of the present invention is a kit for an assay for the analytes buprenorphine (BUP) and/or metabolites of buprenorphine (BUP) comprising in packaged combination:
(i) an antibody raised against the compound of any of the above formulas 1–5; and,
(ii) a conjugate of a derivative of the analytes.

Another embodiment of the present invention is a kit for an assay for the analyte norbuprenorphine (norBUP) comprising in packaged combination:

(i) an antibody raised against any of the above formulas 1–5; and,
(ii) a conjugate of a derivative of the analyte.

Another embodiment of the present invention is a kit for an assay for the analytes norbuprenorphine (norBUP) and/or metabolites of norbuprenorphine (norBUP) comprising in packaged combination:
(i) an antibody raised against any of the above formulas 1–5; and,
(ii) a conjugate of a derivative of the analytes.

Another embodiment of the present invention is a kit for an assay for the analytes buprenorphine (BUP), and/or metabolites of buprenorphine (BUP), and/or norbuprenorphine (norBUP), and/or metabolites of norbuprenorphine (norBUP) comprising in packaged combination:
(i) an antibody raised against any of the above formulas 1–5; and,
(ii) a conjugate of a derivative of the analytes.

Another embodiment of the present invention is a kit for an assay for the analyte buprenorphine (BUP) comprising in packaged combination:
(i) an antibody raised against a derivative of the analyte; and,
(ii) a conjugate of a hapten of the analyte, wherein the hapten is any of the above formulas 1–5.

Another embodiment of the present invention is a kit for an assay for the analytes buprenorphine (BUP) and/or metabolites of buprenorphine (BUP) comprising in packaged combination:
(i) an antibody raised against a derivative of the analyte; and,
(ii) a conjugate of a hapten of the analyte, wherein the hapten is any of the above formulas 1–5.

Another embodiment of the present invention is a kit for an assay for the analyte norbuprenorphine (norBUP) comprising in packaged combination:
(i) an antibody raised against a derivative of the analyte; and,
(ii) a conjugate of a hapten of the analyte, wherein the hapten is any of the above formulas 1–5.

Another embodiment of the present invention is a kit for an assay for the analytes norbuprenorphine (norBUP) and/or metabolites of norbuprenorphine (norBUP) comprising in packaged combination:
(i) an antibody raised against a derivative of the analyte; and,
(ii) a conjugate of a hapten of the analyte, wherein the hapten is any of the above formulas 1–5.

Another embodiment of the present invention is a kit for an assay for the analytes buprenorphine (BUP), and/or metabolites of buprenorphine (BUP), and/or norbuprenorphine (norBUP), and/or metabolites of norbuprenorphine (norBUP) comprising in packaged combination:
(i) an antibody raised against a derivative of the analyte; and,
(ii) a conjugate of a hapten of the analyte, wherein the hapten is any of the above formulas 1–5.

Figure 5:
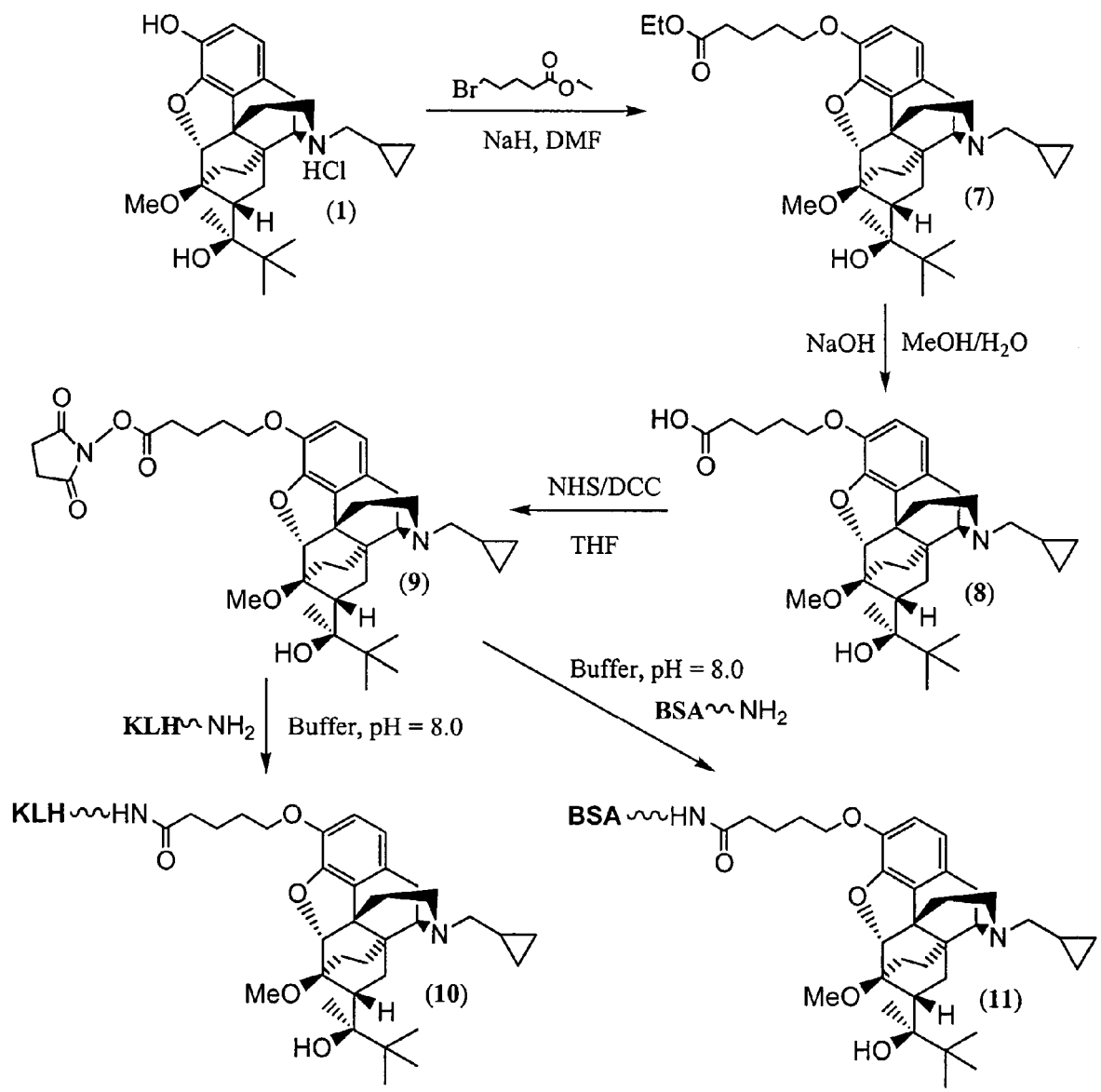
FIG. 5 shows the synthesis of buprenorphine immunogens (10–11) of the present invention.

Syntheses a) Synthesis of Novel Buprenorphine Haptens and Immunogens of the Present Invention The synthesis of buprenorphine immunogens (10) and (11) containing a linker on the hydroxyl group at the benzene ring commenced with an alkylation of commercially available buprenorphine (1) with ethyl 5-bromovalerate followed by hydrolysis of the ester group to generate the acid (8) (FIG. 5). The acid (8) was activated by DCC and NHS ester and followed by a reaction with amines either from KLH (Keyhole Limpet Hemocyanine) or BSA (Bovine Serum Albumin) to give immunogens (10) and (11).

The concentration of KLH immunogen (10) was measured in an BCA (bincinchroninic acid) assay and hapten number determination was determined using the known TNBS (2,4,6-Trinitrobenzesulfonic acid) method. The immunogen (10) had a concentration of 1.54 mg/ml with a hapten number of 1688, and was used for the immunization of sheep, mice and rabbit for antibody production. By the same detection method, the BSA immunogen (11) had a protein concentration of 1.46 mg/ml with a hapten number of 39 and was utilized for antibody production.

Figure 6:
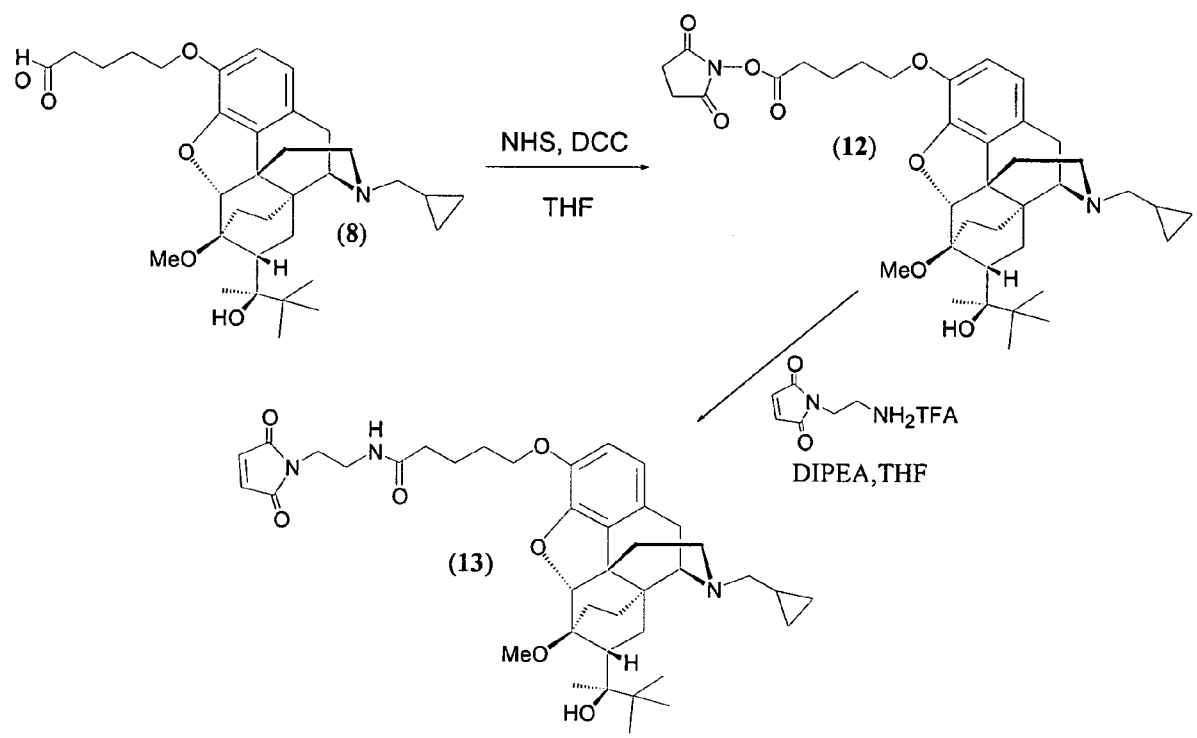
FIG. 6 shows the synthesis of buprenorphine hapten (13) of the present invention.
Figure 7:
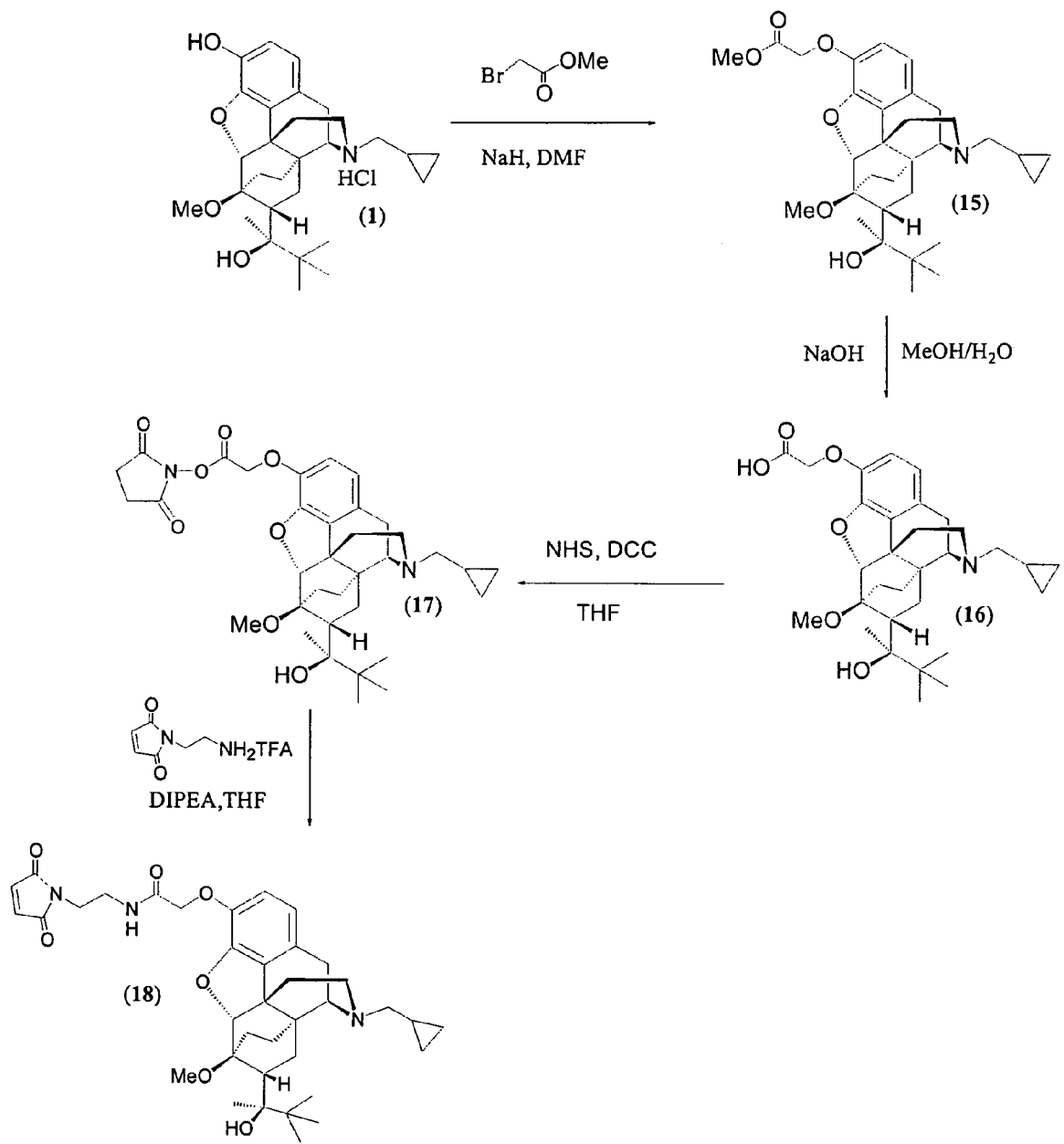
FIG. 7 shows the synthesis of buprenorphine hapten (18) of the present invention.
Figure 8:
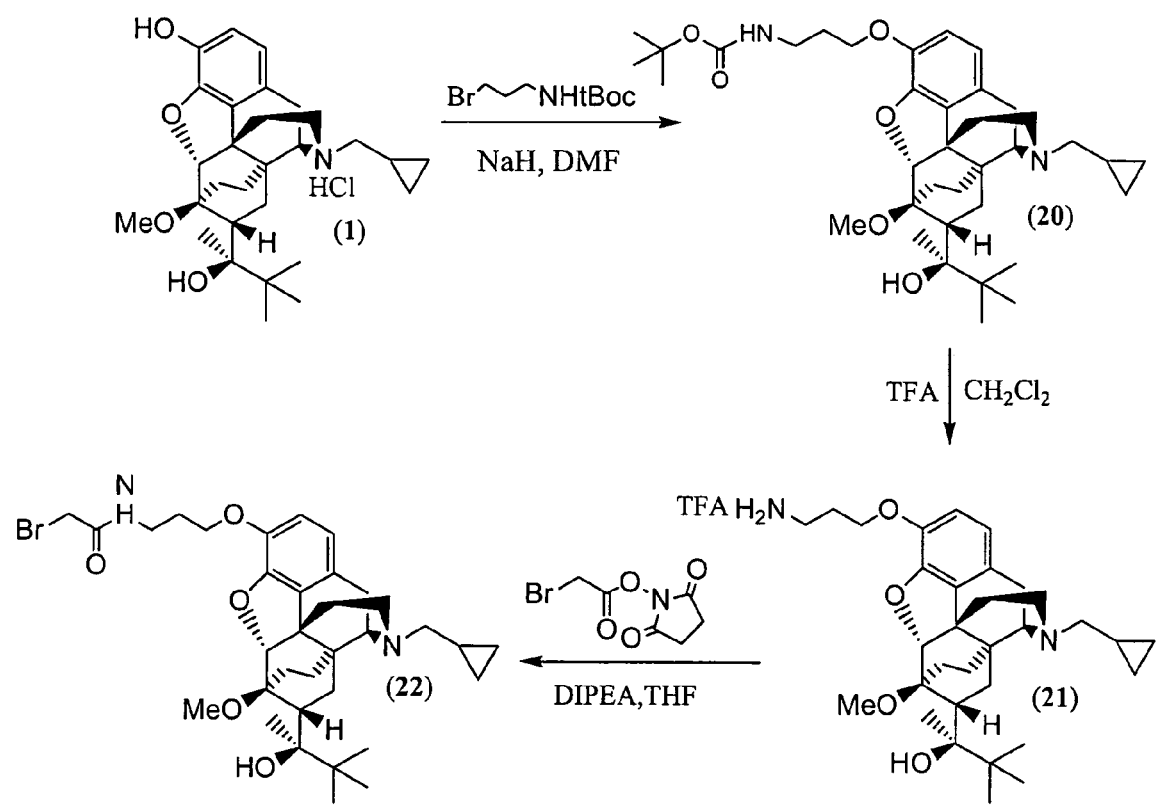
FIG. 8 shows the synthesis of buprenorphine hapten (22) of the present invention.

Several buprenorphine haptens (13, 18, 22) with a different length of linker were designed for mutant G6PDH or bio-conjugation (See FIGS. 6, 7, and 8.). Activation of the acid group of the available compound (8) and subsequent reaction with a linker, maleimidoethyl amine, gave compound (13) (FIG. 6). Compound (13) introduced the maleimide functionality for thiol modification of mutant G6PDH enzyme.

The synthesis of buprenorphine hapten (18) utilized chemistry similar to that described in FIG. 6. Reaction of phenol group from buprenorphine with methyl bromoacetate under basic condition introduced a linker on the hydroxyl group of the benzene ring to give compound (15) (FIG. 7). Hydrolysis of 15 followed by activation of the resulting acid (16) with DCC and NHS gave the desired intermediate 17. Again, reaction of 17 with a linker, maleimidoethyl amine, gave hapten (18).

A buprenorphine hapten (22) with bromoacetamide functionality was designed for reaction with the thiol group from mutant G6PDH protein or a label protein including alkaline phosphatase, B-galactosidase and horse radish peroxidase. The synthesis of hapten (22) started with a reaction of starting material (1) with an available linker, (3-Bromopropyl)-carbamic acid tert-butyl ester, under basic condition (FIG. 8). Removal of the t-Boc protecting group from the linker gave the amine (21). Suitable protecting groups are well known in the art and have been described in detail in numerous patents and articles in the technical literature. See, for example, "Principles of Peptide Synthesis" (M. Bodanszky, Springer Verlag, Berlin, Heidelberg, New York, Tokyo (1984). Examples of such protecting groups, by way of example and not limitation, are t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenxyloxycarbonyl, o-nitrophenylsulfenyl, 2-cyano-1,1-dimentylethoxycarbonyl, bromobenzyloxy, carbamyl, formyl, and the like. The particular protecting group chosen depends on the nature of the reaction to be performed and the conditions of such reaction such as temperature, pH, and so forth. Reaction of (21) with succinimidyl-bromo-acetate under basic condition gave the desired product (22) (FIG. 8).

b) Synthesis of Norbuprenorphine Haptens and Immunogens of the Present Invention The preparation of norbuprenorphine immunogens (33) and (37) required the construction of a linker for enzyme conjugation at the secondary amine or the phenol functional group in norbuprenorphine, respectively . Two synthetic approaches were used for the design and synthesis of immunogens (33) and (37). One was to introduce a linker onto the hydroxyl group on the benzene ring of the norbuprenorphine molecule by an alkylation reaction (See FIGS. 9 and 10.). The other was to modify the amine nitrogen by an acylation reaction (See FIGS. 11, 12, 13.).

Figure 9:
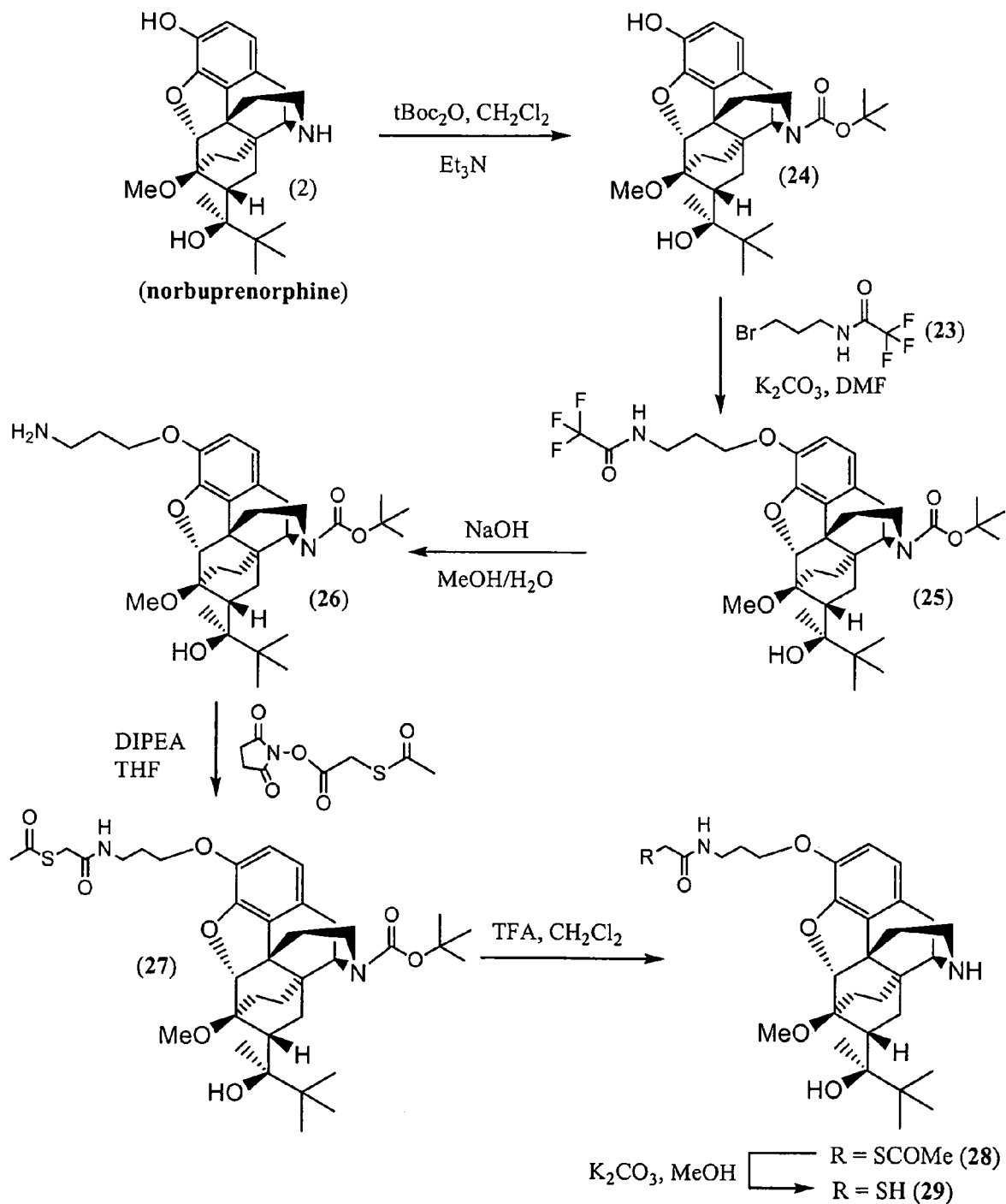
FIG. 9 shows the synthesis of norbuprenorphine hapten (29) of the present invention.
Figure 10:
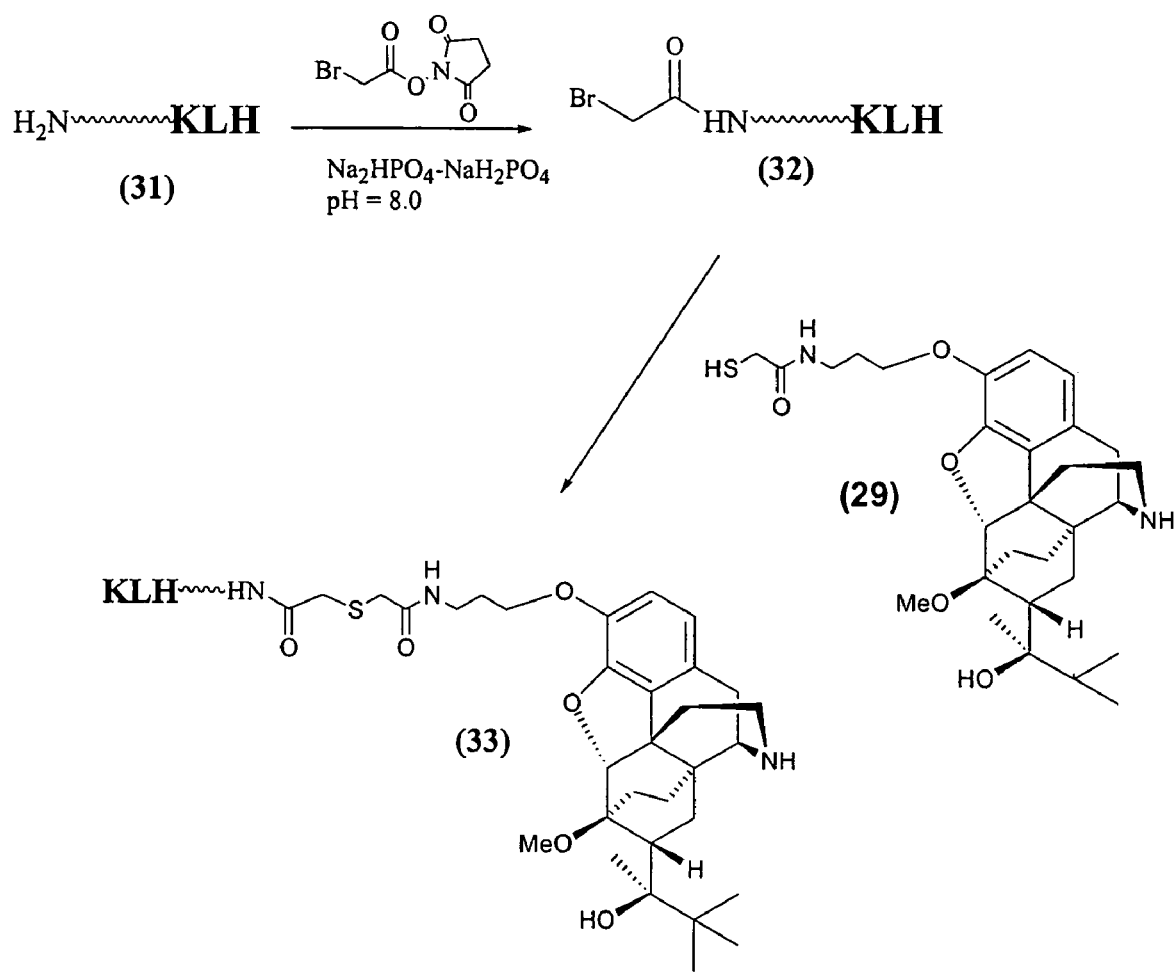
FIG. 10 shows the synthesis of norbuprenorphine KLH immunogen (33) of the present invention.

The synthesis of hapten (29) and immunogen (33) whereby a modification occurred at the phenol functional group of norbuprenorphine is shown in FIGS. 9 and 10. The thiol (—SH) chemistry was utilized to attach to the protein based on the fact that thiol is a stronger nucleophile than the secondary amine of norbuprenorphine. In contrast, amine is a stronger nucleophile than phenol so that selective protecting of the amine group of norbuprenorphine was essential for the introduction of a linker at the phenol site. Thus, the synthesis of 29 commenced with the selective protection of the secondary amine with t-butyl anhydride to give compound (24) (See FIG. 7.). Alkylation of phenol (24) with a linker (23) containing a trifluroacetamide group gave compound (25). Selective removal of the trifluroacetamide group of 25 under basic condition followed by reaction of the commercially available linker, 2-Mercapto[S-acetyl]acetic acid N-hydroxysuccinimide ester, gave compound (27). Reaction of 27 with trifluoroacetic acid selectively deprotected the t-Boc group to give the amine-thiol acetate which could be hydrolyzed to the desired thiol (29) (See FIG. 9.). The thiol (29) was used for preparation of immunogen (33) and G6PDH conjugation.

The synthesis of norbuprenorphine immunogen (33) through a linker onto the hydroxyl group on the benzene ring is shown in FIG. 10. Reaction of amines from keyhole limpet hemocyanin (KLH) with succinimidyl-bromo-acetate introduced the bromo-acetamide group for thiol modification. Reaction of thiol (29) with the modified KLH (31) in sodium phosphate (0.1 M, pH=8.0) buffer solution gave the desired immunogen (33). The immunogen (33) was purified on a sephadex G-25 column with buffer solution. The concentration of immunogen (33) was measured using BCA Protein Assay and the TNBS method was used for hapten number determination. The immunogen (33) had a concentration of 0.96 mg/ml with a hapten number of 1280, and was used for the immunization of mice, rabbits and sheep for antibody production.

Figure 12:
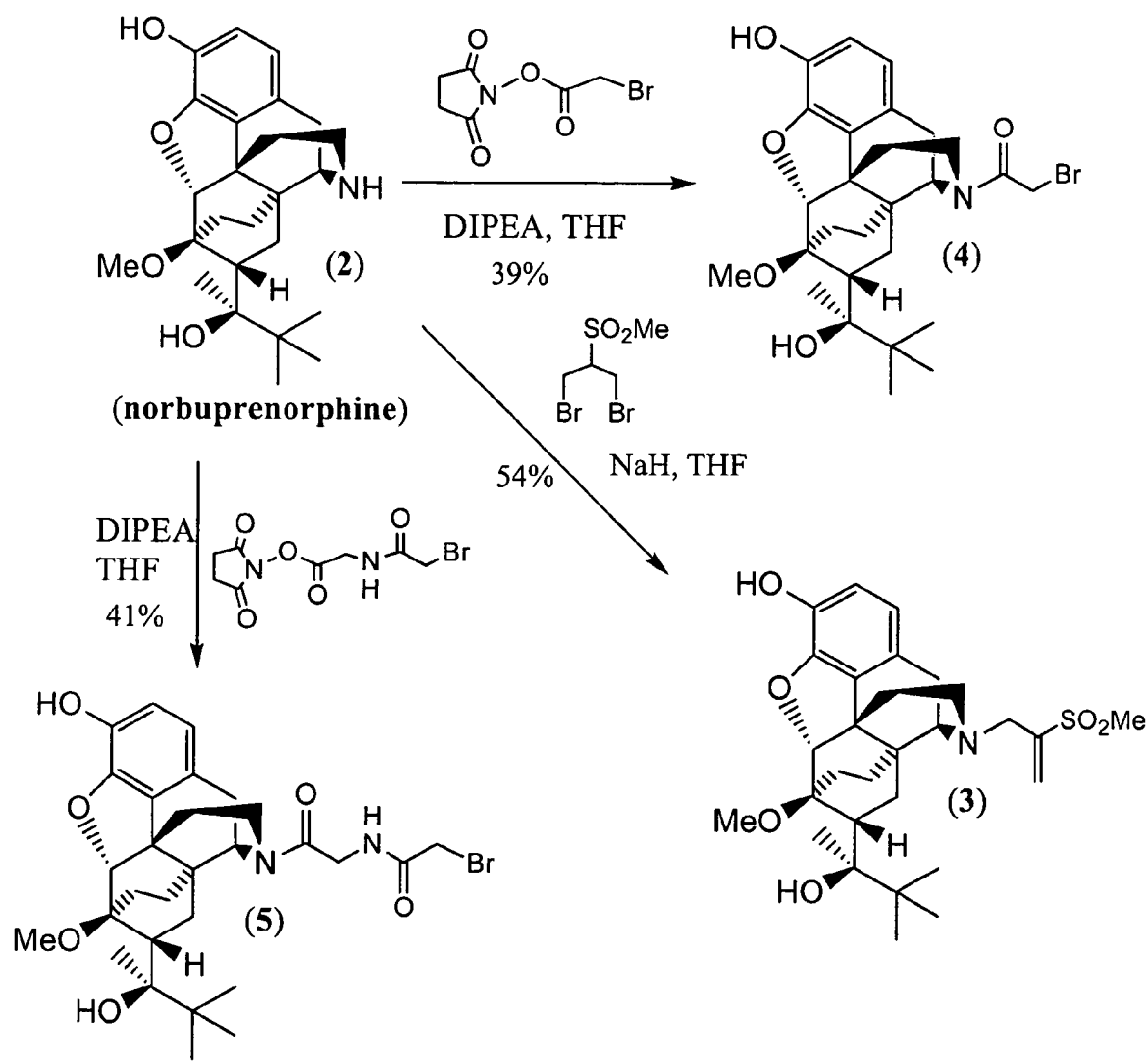
FIG. 12 shows the synthesis of buprenorphine haptens (3, 4, 5) of the present invention.

The norbuprenorphine haptens (3–5) were designed for Mutant G6PDH conjugation. The synthesis of haptens (3–5) is shown in FIG. 12. Reaction of 1,3-dibromo-2-(methylsulfonyl)-propane with norbuprenorphine in the presence of sodium hydride gave hapten (3). Acylation of norbuprenorphine (2) with bromoacetic N-hydroxyl succinimide under basic condition gave hapten (4). Using similar chemistry, norbuorenorphine hapten (5) was prepared (FIG. 12).

Figure 11:
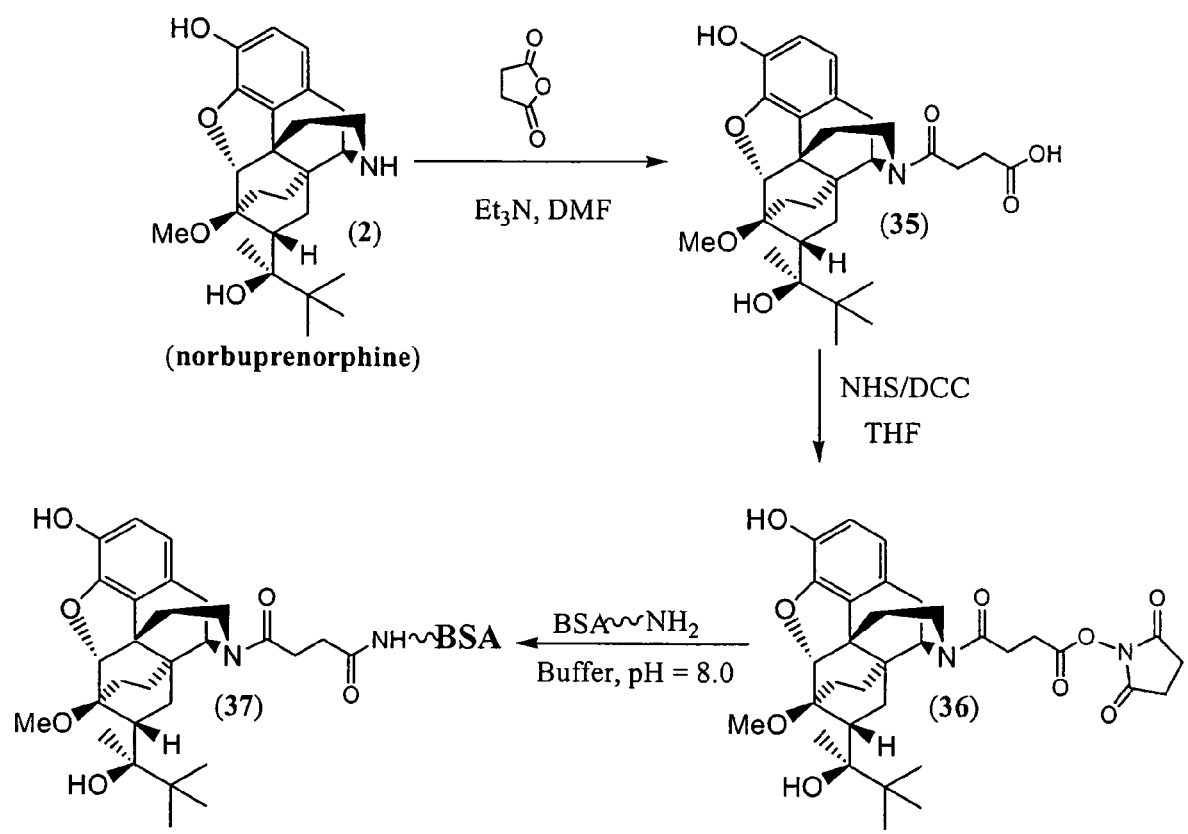
FIG. 11 shows the synthesis of norbuprenorphine BSA immunogen (37) of the present invention.
Figure 13:
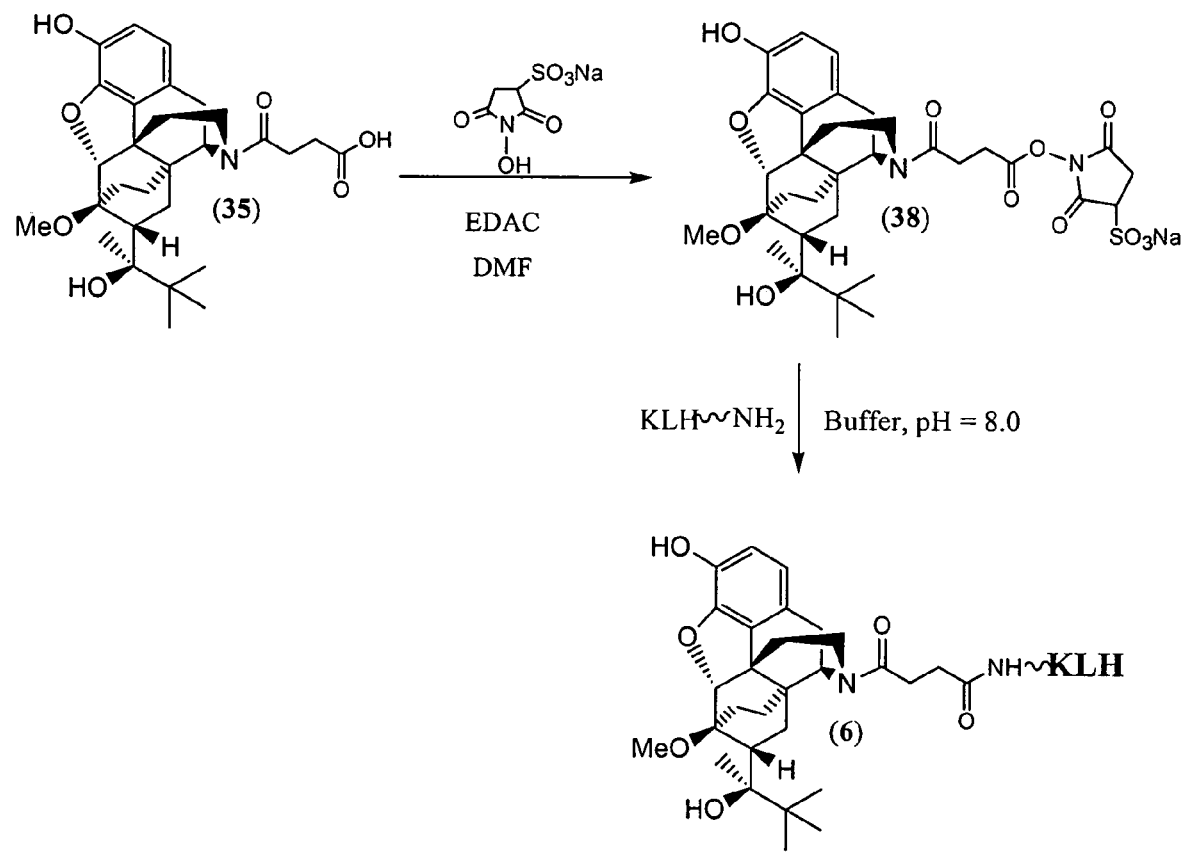
FIG. 13 shows the synthesis of buprenorphine immunogen (6) of the present invention; and, FIG. 14 shows an antibody screening technique useful with the present invention.

The synthesis of immunogen (37) is shown in FIG. 11. Acylation of succinic anhydride with norbuprenorphine (2) occurred at the secondary amine to give acid (35). Again, the acid (35) was activated by DCC and NHS ester followed by a reaction with amines from BSA to give the desired immunogen (37). The concentration of immunogen (37) was measured by BCA Protein Concentration Assay. The immunogen (37) had a concentration of 1.0 mg/ml with a hapten number of 33, and was used for the immunization of mice and rabbit for antibody production. Similar chemistry has been used for preparation of KLH immunogen (6) (FIG. 13).

All the prepared haptens and immunogens (3, 4, 5, 13, 18, 22 and 29) were used for G6PDH bio-conjugation. The immunogens (6, 10, 11, 33 and 37) were used for elicitation of specific antibodies. All immunogens (6, 10, 11, 33 and 37) were used to raise antibodies. In an enzyme-based assay format, antibodies showed good modulation with both buprenorphine and norbuprenorphine free drugs. The fact that all immunogens (6, 10, 11, 33, and 37) successfully raised antibodies and showed potential use in an enzyme-based buprenorphine immunoassay indicates that a mediate linker (4–7 atomic length) facilitates well with the immunization process.

Preparation of Antibodies

The following method may be employed to prepare polyclonal antibodies using any of the new immunogens seen in Formulas I–V. Antiserum containing antibodies is obtained by well-established techniques involving immunization of an animal, such as rabbits and sheep, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

The following procedure may be employed to prepare monoclonal antibodies, in particular for the immunogens of Formulas 1–5. Monoclonal antibodies were produced according to the standard techniques of Köhler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of an non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In general, antibodies can be purified by known techniques such as chromatography, e.g., DEAE chromatography, ABx chromatography, and the like, filtration, and so forth. Antibodies may be screened using any of several techniques, for example using an Emit® assay format as illustrated in FIG. 14, and considering such properties as specificity, conjugate inhibition, curve size and cross-reactivity.

Experimental Details

General Method Analytical thin layer chromatography (TLC) was the usual analysis method and performed on Analtech Uniplate Silica Gel GF (0.25 mm) glass-backed plates using the specified solvent. The spots on TLC were visualized by ultraviolet light (short and/or long wave) and/or iodine vapors. Flash chromatography was carried out on Whatman silica gel 60 Å (230–400 mesh). All chemicals were obtained from Sigma, Aldrich, Fluka or Lancaster and used as received. H-NMR and C-NMR spectra routinely recorded on a Bruker Ultrashiel™-400 (400 MHz) spectrometer. Chemical shift were reported in parts per million (ppm, δ) and related to tetramethylsilane or with deuterated solvent as the internal reference. NMR abbreviations used are s (singlet), d (doublet), and m (multiplet).

Preparation of Compound (3)

See FIG. 12. To a solution of norbuprenorphine (2) (18.8 mg, 0.0455 mmol) in THF (4.0 mL) were added NaH (12 mg, 0.475 mmol). The reaction mixture was stirred at 0° C. for 20 minutes. A solution of 1,3-dibromo-2(methylsulfonyl)propane (13 mg, 0.0464 mmol) in THF (1 mL) was added to the mixture. The reaction was stirred at room temperature for 1 hour. Water (10 mL) was added and most of THF was removed by rotary evaporation. The aqueous phase was extracted with EtOAc (3×20 mL). The combined organic phase was washed with water (10 mL) and dried over $MgSO_4$. The organic phase was filtered and concentrated to dryness. The residue was purified by flash column chromatography (silica gel) using ethyl acetate/hexane (2/3) as an eluent to give compound (3) (13.2 mg, 54%) FAB-MS m/z: 532 ($M^+$, 72); $^1$H-NMR ($CDCl_3$, 400 MHz) δ: 6.70 (d, J=8.0 Hz, 1H), 6.53 (d, J=8.0 Hz, 1H), 5.97 (s, 1H), 5.85 (s, 1H), 4.46 (m, 1H), 3.54–3.60 (m, 1H), 3.51 (s, 3H), 3.30 (m 1H), 3.05–3.06 (m, 1H), 3.03 (s, 3H), 2.85 (m, 1H), 2.55–2.75 (m 2H), 2.33–2.38 (m, 2H), 2.10 (m, 1H), 1.70–1.95 (m, 5H), 1.40 (m, 1H), 1.33 (s, 3H), 0.98 (m, 11H), 0.71 (m, 1H). $^{13}$C-NMR ($CDCl_3$, 400 MHz) δ: 147.6, 145.9, 137.9, 132.2, 128.0, 127.8, 120.2, 117.2, 97.1, 80.9, 79.7, 61.4, 56.3, 53.0, 46.4, 44.1, 43.1, 40.8, 36.7, 35.5, 34.0, 29.8, 26.7, 24.0, 20.5, 18.4; HRMS: $C_{29}H_{42}NO_6S$ Calculated: 532.2732 ($MH^+$); Found: 532.2742.

Preparation of Compound (4)

See FIG. 12. To a solution of norbuprenorphine (2) (40 mg, 0.0967 mmol) in THF (10 mL) were added diisopropylethylamine (33 uL, 25 mg, 0.189 mmol) and a solution of bromoacetic N-hydroxyl succinimide (27 mg, 0.108 mmol) in THF (5 mL) at 0° C. under argon. The reaction was stirred at room temperature for 2 hours. Water (10 mL) was added and most of THF was removed by rotary evaporation. The aqueous phase was extracted with $CH_2Cl_2$ (3×30 mL). The combined organic phase was washed with water (15 mL) and dried over $MgSO_4$. The organic phase was filtered and concentrated to dryness. The residue was purified by flash column chromatography (silica gel) using ethyl acetate/hexane (2/3) as an eluent to give compound (4) (20 mg, 39%) FAB-MS m/z: 534 ($M^+$, $^{79}$Br, 100); 536 ($M^+$, $^{81}$Br, 91); $^1$H-NMR ($CDCl_3$, 400 MHz) δ: 6.73 (d, J=8.0 Hz, 1H), 6.53 (d, J=8.0 Hz, 1H), 5.84 (m, 1H), 4.75 (m, 1H), 4.43 (m, 2H), 3.80–4.08 (m, 2H), 3.60 (m 1H), 3.51 (s, 3H), 3.30 (m 1H), 2.60–3.0 (m, 3H), 2.05–2.20 (m, 3H), 1.80 (m, 2H), 1.48 (m, 1H), 1.31 (s, 3H), 0.96 (m, 10H), 0.73 (m, 1H); HRMS:$C_{27}H_{37}BrNO_5$ Calculated: 534.1854($MH^+$, $^{79}$Br), 536.1834($MH^+$, $^{81}$Br), Found: 534.1835, 536.1826.

Preparation of Compound (5)

See FIG. 12. To a solution of norbuprenorphine (2) (25 mg, 0.0604 mmol) in THF (5 mL) were added diisopropylethyl-amine (21 uL, 15 mg, 0.116 mmol) and a solution of bromoacetylglycine N-hydroxyl succinimide ester (21 mg, 0.07 mmol) in THF (2 mL) at 0° C. under argon. The reaction was stirred at room temperature for 1 hour. Water (5 mL) was added and most of THF was removed by rotary evaporation. The aqueous phase was extracted with EtOAc (3×20 mL). The combined organic phase were washed with water (10 mL) and dried over $MgSO_4$. The organic phase was filtered and concentrated to dryness. The residue was purified by flash column chromatography (silica gel) using ethyl acetate/hexane (2/3) as an eluent to give compound (5) (15 mg, 42%). FAB-MS m/z: 597 ($MLi^+$, $^{79}$Br, 80); 599 ($MLi^+$, $^{81}$Br, 80); $^1$H-NMR ($CDCl_3$, 400 MHz) δ: 7.64–7.55 (m, 1H), 6.77 (d, J=8.1 Hz, 1H), 6.55 (d, J=8.12 Hz, 1H), 5.75 (d, J=6.78 Hz, 1H), 4.78 (d, J=6.98 Hz, 1H), 4.44 (m, 1H), 3.90–4.20 (m, 2H), 3.90 (s, 2H), 3.70 (m 1H), 3.51 (s, 3H), 2.70–3.20 (m 3H), 2.00–2.15 (m, 2H), 1.75–1.90 (m, 4H), 1.32–1.60 (m, 1H), 1.31 (s, 3H), 1.1–1.25 (m, 1H), 0.95 (m, 10H), 0.72 (m, 1H). See FIG. 12.

Preparation of KLH-Immunogen (6)

See FIG. 13. To a solution of (35) (9 mg, 0.0175 mmol) in DMF (0.8 mL) was added EDAC (11 mg, 0.0573 mmol) and sulfo-NHS ester (15.2 mg, 0.07 mmol). The reaction was stirred at room temperature under argon for 16 hours. The complete reaction was observed by checking TLC (silica gel, $MeOH/CH_2Cl_2$=1/4). The activated hapten (38) was added dropwise under argon to 8 mL of 2.5 mg/mL of KLH Sodium phosphate solution (0.1M, pH=8.0) at 0° C. under argon. The pH value changed during the addition and 0.1 M of NaOH aqueous solution was used to adjust the pH=8.0. After completed the addition, the conjugate was allowed to stir at room temperature for 1.5 hours. The conjugate was dialyzed against Dulbecco's phosphate buffered saline (pH=7.0, 3 Liters) prepared from Dulbecco's phosphate buffered saline (Sigma buffer, 400 mL) diluting with DE water (2600 mL) at 4° C. for 4 hours. The dialyzing procedure was repeated with fresh buffer solution for 16, 24 and 40 hours. Finally, the conjugate was dialyzed with sodium phosphate buffer solution (10 mM, pH=7.0) two times (3 hours and 4 hours). The concentration of protein was measured by using BCA Protein Concentration Assay and the TNBS method was used for hapten number determination. The conjugate has a concentration of 2.21 mg/mL with the hapten numberof 1142. See FIG. 13.

Preparation of Compound (7)

See FIG. 5. To a suspension of buprenorphine hydrochloride (1) (50 mg, 0.099 mmol) in DMF (5 ml) was added NaH (30 mg, 1.19 mmol). The mixture was stirred at room temperature for 20 minutes. Ethyl 5-bromovalerate (0.10 ml, 0.631 mmol) was added to the mixture and the reaction mixture was stirred at room temperature for 48 hours. DMF was removed by rotary evaporation to dryness. The residue was purified by flash column chromatography (silica gel) using hexane/ethyl acetate (1/1) as the eluent to give compound (7) (57 mg, 96%). $^1$H-NMR ($CDCl_3$, 400 MHz) δ: 6.70 (d, J=8.0 Hz, 1H), 6.53 (d, J=8.0 Hz, 1H), 5.93 (s, 1H), 4.41 (s, 1H), 4.15 (m, 4H), 3.54 (s, 3H), 2.99 (m, 2H), 2.90 (m, 1H), 2.58 (m, 1H), 2.30–2.37 (m, 8H), 1.80 (m, 6H), 1.36 (s, 3H), 1.25 (m, 5H), 1.04 (m, 10H), 0.80 (m, 1H), 0.72 (m, 1H), 0.49 (m, 2H), 0.12 (m, 2H). See FIG. 5.

Preparation of Compound (8)

To a solution of (7) (57 mg, 0.0956 mmol) in MeOH (4.0 ml) and $H_2O$ (0.4 ml) was added NaOH (100 mg, 2.5 mmol). The reaction mixture was stirred at 55° C. for 1 hour. MeOH was evaporated by rotary evaporation under reduced pressure and the residue was dissolved in $CH_2Cl_2$ (50 ml) and water (10 ml). HCl (2N) was added to the mixture to adjust the pH to 2. The organic solvent was separated and washed with water (2×10 ml). The organic phase was dried over $Na_2SO_4$, filtered and evaporated to dryness. The residue was put in high vacuum to give the desired product (8) (49 mg, 85% yield). $^1$H-NMR (CDCl$_3$, 400 MHz) δ: 6.73 (d, J=8.0 Hz, 1H), 6.56 (d, J=8.0 Hz, 1H), 6.05 (s, 1H), 4.44 (s, 1H), 4.15 (m, 1H), 4.06 (m, 1H), 3.54 (s, 3H), 3.42 (t, J=6.8 Hz, 1H), 3.00 (m, 1H), 2.38 (m, 5H), 2.17 (m, 1H), 1.76–2.01 (m, 10H), 1.50 (m, 1H), 1.36 (s, 3H), 1.26 (m, 3H), 1.03 (m, 10H), 0.90 (m, 1H), 0.79 (m, 1H), 0.56 (m, 2H), 0.2 (m, 2H). See FIG. 5.

Preparation of KLH Immunogen (10)

To a solution of (8) (38 mg, 0.0629 mmol) in THF (3.0 mL) was added DCC (25 mg, 0.121 mmol) and NHS (18 mg, 0.156 mmol). The reaction was stirred at room temperature for 16 hours. The precipitate from the reaction was filtered off and THF was removed by rotary evaporation. The activated hapten (9) was dissolved in DMF (0.8 ml).

To a solution of KLH (20 mg, 8 ml, pH=8.00) was added the above activated hapten solution slowly at 4° C. under nitrogen. The pH value was maintained at 8.0. The reaction was stirred at 4° C. (cold room) for 16 hours. The reaction mixture was separated on a Sephadex G-25 column and eluted with NaH$_2$PO$_4$—Na$_2$HPO$_4$ buffer (pH=7.0, 0.1 M). The UV detector at 280 nm monitored the eluted fractions from the column. A clean separation between KLH immunogen and the hapten was obtained. Fractions containing protein were pooled and concentrated to 20 ml. The concentration of immunogen was measured by using BCA Protein Concentration Assay. The immunogen (10) had a concentration of 1.54 mg/ml with a hapten number of 1688, and was used for the immunizations. See FIG. 5.

Preparation of BSA Immunogen (11)

To a solution of 8 (39 mg, 0.0646 mmol) in THF (3 mL) was added DCC (24 mg, 0.116 mmol) and NHS (17 mg, 0.1477 mmol). The reaction was stirred at room temperature for 16 hours. The precipitate from the reaction was filtered off and THF was removed by rotary evaporation. The activated hapten (9) was dissolved in DMF (0.8 ml).

To a solution of BSA (40 mg, 8 ml, pH=8.00) was added the above activated hapten solution slowly at 4° C. under nitrogen. The pH value was maintained at 8.0. The reaction was stirred at 4° C. (cold room) for 16 hours. The reaction mixture was separated on a Sephadex G-25 column and eluted with NaH$_2$PO$_4$—Na$_2$HPO$_4$ buffer (pH=7.0, 0.1 M). The UV detector at 280 nm monitored the eluted fractions from the column. A clean separation between BSA immunogen and the hapten was obtained. Fractions containing protein were pooled and concentrated to 25 ml. The concentration of BSA immunogen was measured by using BCA Protein Concentration Assay. The BSA immunogen (11) had a concentration of 1.46 mg/ml with a hapten number of 39, and was used for the immunizations. See FIG. 5.

Preparation of Compound (13)

To a solution of (8) (40 mg, 0.0662 mmol) in THF (5 ml) was added DCC (28 mg, 0.135 mmol) and NHS (19 mg, 0.165 mmol). The reaction mixture was stirred at room temperature for 16 hours. The precipitate from the reaction was filtered off and washed with anhydrous THF (5 ml). TLC analysis of the mixture showed that a less polar spot displayed in comparison with 8. To this solution was added diisopropylethylamine (0.2 ml, 1.15 mmol) and 2-maleimidoethylamine trifluoroacetic acid (42 mg, 0.165 mmol). The reaction was stirred at room temperature for 2 hours. Water (10 ml) was added and most of THF was evaporated by rotary evaporation. The aqueous phase was extracted with ethyl acetate (3×30 ml). The combined organic phase was washed with water (10 ml), dried over Na$_2$SO$_4$, filtered and evaporated to dryness. The residue was purified by flash column chromatography (silica gel) using ethyl acetate/hexane (9/1) to give the desired product (13) (4.8 mg). $^1$H-NMR (CDCl$_3$, 400 MHz) δ: 6.69 (d, J=8.0 Hz, 1H), 6.68 (s, 2H), 6.55 (d, J=8.0 Hz, 1H), 6.15 (m, 1H), 5.89 (s, 1H), 4.43 (s, 1H), 4.14 (m, 3H), 4.06 (m, 1H), 3.75 (m, 2H), 3.53 (s, 3H), 3.49 (m, 4H), 3.03 (m, 2H), 2.91 (m, 1H), 2.65 (m, 1H), 2.30 (m, 7H), 1.60 (m, 2H), 1.37 (s, 3H), 1.26 (m, 3H), 1.05 (m, 9H), 0.91 (m, 2H), 0.73 (m, 1H), 0.53 (m, 2H), 0.15 (m, 2H). See FIG. 6.

Preparation of Compound (15)

To a solution of buprenorphine hydrochloride (1) (100 mg, 0.198 mmol) in DMF (4 ml) was added NaH (50 mg). The reaction mixture was stirred at room temperature for 20 minutes. Methyl bromoacetate (46.5 mg) was added to the mixture. The mixture was stirred at room temperature for 4 hours. DMF was removed by rotary evaporation and water (5 mL) was added. The aqueous phase was extracted with ethyl acetate (3×30 ml). The combined organic phases were washed with water (15 ml), dried over MgSO$_4$, filtered and concentrated. The residue was purified by flash column chromatography using ethyl acetate/hexane (1/1) as the eluent to give the desired product (15) (28 mg); $^1$H-NMR (CDCl$_3$, 400 MHz) δ: 6.77 (d, J=8.0 Hz, 1H), 6.55 (d, J=8.0 Hz, 1H), 5.89 (s, 1H), 4.79 (dd, J=16, 20 Hz, 2H), 4.44 (s, 1H), 3.79 (s, 3H), 3.53 (s, 3H), 2.99 (m, 2H), 2.90 (m, 1H), 2.61 (m, 1H), 2.37–2.13 (m, 5H), 1.80 (m, 2H), 1.67 (m, 2H), 1.38 (s, 3H), 1.28 (m, 2H), 1.05 (m, 9H), 0.80 (m, 1H), 0.72 (m, 1H), 0.50 (m, 2H), 0.12 (m, 2H). See FIG. 7.

Preparation of Compound (16)

To a solution of (15) (28 mg, 0.05188 mmol) in MeOH (4 mL) and H$_2$O (1.0 mL) was added NaOH (100 mg). The reaction mixture was stirred at room temperature for 1 hour and at 50° C. for 0.5 hour. Most of MeOH were removed by rotary evaporation. Water (5 ml) and HCl (3N) was added to the mixture to maintain the pH at 3.0. The aqueous phase was extracted with CH$_2$Cl$_2$ (3×30 ml). The combined organic phase was washed with water (10 ml) and dried over MgSO$_4$. The organic phase was filtered and concentrated to dryness. The residue was put in high vacuum to give the desired product (16) (27 mg, 93% yield); $^1$H-NMR (CD$_3$OD, 400 MHz) δ: 6.68 (m, 1H), 6.52 (m, 1H), 5.86 (m, 1H), 4.54 (m, 2H), 4.20 (s, 1H), 3.53 (s, 3H), 2.99 (m, 2H), 2.90 (m, 3H), 2.53 (m, 1H), 2.37–2.13 (m, 5H), 1.82–1.64 (m, 4H), 1.39–1.28 (m, 5H), 1.05 (m, 9H), 0.80 (m, 1H), 0.72 (m, 1H), 0.50 (m, 2H), 0.12 (m, 2H). See FIG. 7.

Preparation of Compound (18)

To a solution of (16) (27 mg, 0.048 mmol) in THF (3.0 mL) was added DCC (20 mg, 0.0969 mmol) and NHS (14 mg, 0.121 mmol). The reaction was stirred at room temperature for 16 hours. The precipitate from the reaction was filtered off and anhydrous THF (3 ml) was used to wash the precipitate. The combined THF solution was used for the next reaction. To this solution was added diisopropyl-ethylamine (200 uL, 148 mg, 1.15 mmol) and 2-maleimidoethylamine trifluoroacetic acid (30 mg, 0.118 mmol). The reaction was stirred at room temperature for 2 hours. Water (10 ml) was added and most of THF was evaporated by rotary evaporation. The aqueous phase was extracted with ethyl acetate (3×30 ml). The combined organic phase was washed with water (10 ml), dried over Na$_2$SO$_4$, filtered and evaporated to dryness. The residue was purified by flash column chromatography (silica gel) using ethyl acetate/hexane (9/1) to give the desired product (18) (11 mg, 35% yield). $^1$H-NMR (CDCl$_3$, 400 MHz) δ: 7.05 (m, 1H), 6.73 (d, J=8.0 Hz, 1H), 6.72 (s, 2H), 6.55 (d, J=8.0 Hz, 1H), 5.85

(s, 1H), 4.56 (dd, J=16, 20 Hz, 2H), 4.44 (s, 1H), 4.13 (s, 1H), 4.12 (m, 4H), 3.74 (m, 2H), 3.55 (m, 3H), 3.00 (m, 2H), 2.92 (m, 1H), 2.63 (m, 1H), 2.39–2.10 (m, 4H), 1.80 (m, 2H), 1.67 (m, 2H), 1.38 (s, 3H), 1.04 (m, 9H), 0.80 (m, 1H), 0.72 (m, 1H), 0.50 (m, 2H), 0.12 (m, 2H). See FIG. 7.

Preparation of Compound (20)

To a solution of buprenorphine hydrochloride (1) (50 mg, 0.099 mmol) in DMF (5 ml) was added NaH (35 mg, 1.458 mmol). The reaction mixture was stirred at room temperature for 20 minutes. (3-Bromo-propyl)-carbamic acid tert-butyl ester (180 mg, 0.756 mmol) was added to the mixture. The mixture was stirred at room temperature for 20 hours. DMF was removed by rotary evaporation to dryness. The residue was purified by flash column chromatography using ethyl acetate/hexane (7/3) as an eluent to give the desired product (20) (47 mg, 76% yield); $^1$H-NMR (CDCl$_3$, 400 MHz) δ: 6.72 (d, J=8.0 Hz, 1H), 6.55 (d, J=8.0 Hz, 1H), 5.92 (s, 1H), 4.93 (m, 1H), 4.43 (s, 1H), 4.12 (m, 2H), 3.55 (s, 3H), 3.31 (m, 2H), 3.00 (m, 2H), 2.92 (m, 1H), 2.62 (m, 1H), 2.39–2.10 (m, 5H), 1.95–1.90 (m, 3H), 1.81 (m, 2H), 1.70 (m, 1H), 1.45 (s, 10H), 1.37 (s, 3H), 1.05 (s, 10H), 0.83 (m, 1H), 0.72 (m, 1H), 0.52 (m, 2H), 0.13 (m, 2H). See FIG. 8.

Preparation of Compound (21)

To a solution of (20) (47 mg, 0.0752 mmol) in CH$_2$Cl$_2$ (2 ml) was added TFA (0.4 mL). The reaction mixture was stirred at room temperature for 1 hour. TLC analysis of the reaction showed that starting material (20) disappeared and a new more polar spot displayed (silica gel, ethyl acetate/hexane=7/3). Most of CH$_2$Cl$_2$ and TFA were removed by rotary evaporation under reduced pressure. The residue was further dried under high vacuum to remove a trace of TFA for 2 hours. This gave the desired product (21) used for next reaction without further purification. See FIG. 8.

Preparation of Compound (22)

Compound (21) was dissolved in anhydrous THF (3 ml). To this solution was added diisopropyl-ethylamine (0.7 mL, 4.02 mmol) and the mixture was stirred for 0.5 hour. Bromoacetic N-hydroxyl succinimide (36 mg, 0.152 mmol) was added to the mixture. The reaction was stirred at room temperature for 2 hours. Most of the THF was evaporated by rotary evaporator to dryness. The residue was purified by flash column chromatography (silica gel) using ethyl acetate to give the desired product (22) (12 mg, 25% yield in two step reactions). $^1$H-NMR (CDCl$_3$, 400 MHz) δ: 7.02 (m, 1H), 6.76 (d, J=8.0 Hz, 1H), 6.56 (d, J=8.0 Hz, 1H), 5.87 (s, 1H), 4.45 (s, 1H), 4.20 (m, 2H), 3.89 (s, 2H), 3.54 (s, 3H), 3.51 (m, 2H), 3.00 (m, 2H), 2.90 (m, 1H), 2.66 (m, 1H), 2.36–2.27 (m, 5H), 2.01 (m, 3H), 1.81–1.65 (m, 3H), 1.38 (m, 1H), 1.33 (s, 3H), 1.06 (s, 10H), 0.85 (m, 1H), 0.75 (m, 1H), 0.51 (m, 2H), 0.12 (m, 2H). See FIG. 8.

Preparation of Compound (23)

To a suspension of 3-bromopropyl amine hydrochloride (5.0 g) in CH$_2$Cl$_2$ (80 ml) was added Et$_3$N (7.5 ml). The reaction mixture was stirred at room temperature for 15 minutes. Trifluo-acetic anhydride (4.5 ml) was added to the mixture. The reaction mixture was stirred at room temperature for 16 hours. Water (40 ml) was added. The organic phase was separated and the aqueous phase was extracted with in CH$_2$Cl$_2$ (3×50 ml). The combined organic phase was washed with water (60 ml) and dried over MgSO$_4$. The solvent was filtered and concentrated. The residue was purified by flash column chromatography using ethyl acetate/hexane=(3/7) as an eluent to give the desired product (23) (1.5 g); $^1$H-NMR (CDCl$_3$, 400 MHz) δ: 7.32 (m, 1H), 3.53 (t, J=8 Hz, 2H), 3.42 (t, J=6 Hz, 2H), 2.16 (m, 2H). See FIG. 9.

Preparation of Compound (24)

To a solution of norbuprenorphine hydrochloride (2) (360 mg, 0.8 mmol) in THF (20.0 ml) and H$_2$O (2.0 ml) was added NaHCO$_3$ (800 mg, 9.5 mmol) and t-Boc$_2$O (523 mg, 2.4 mmol). The reaction mixture was stirred at room temperature for 1 hour. TLC analysis of the mixture (silica gel, ethyl acetate/hexane=1/1) showed that a more polar spot displayed as a product in comparison with norbuprenorphine (2). THF was removed by rotary evaporation and water (20 ml) was added. The aqueous was extracted with CH$_2$Cl$_2$ (4×40 ml). The combined organic phase was washed with water (20 ml), dried over MgSO$_4$, filtered and concentrated. The residue was purified by flash column chromatography using ethyl acetate/hexane=(1/1) as the eluent to give the desired product (24) (388 mg, 94% yield); $^1$H-NMR (CDCl$_3$, 400 MHz) δ: 6.75 (d, J=8.0 Hz, 1H), 6.57 (d, J=8.0 Hz, 1H), 5.84 (m, 1H), 5.31 (m, 1H), 4.44 (m, 1H), 4.35 (m, 1H), 4.12 (m, 1H), 3.54 (s, 3H), 3.05–2.85 (m, 3H), 2.10 (m, 2H), 1.70–1.95 (m, 4H), 1.49 (s, 9H), 1.35 (s, 3H), 1.15 (m, 1H), 1.01 (s, 9H), 0.71 (m, 1H). See FIG. 9.

Preparation of Compound (25)

To a solution of 24 (388 mg, 0.755 mmol) in DMF (15 ml) was added K$_2$CO$_3$ (1.5 g). The reaction mixture was stirred at room temperature for 20 minutes. Compound (23) (1.1 g, 4.7 mmol) was added to the mixture. The mixture was stirred at room temperature for 16 hours. DMF was removed by rotary evaporation and water (10 mL) was added. The aqueous phase was extracted with ethyl acetate (4×30 ml). The combined organic phases were dried over MgSO$_4$, filtered and concentrated. The residue was purified by flash column chromatography using ethyl acetate/hexane (4/6) as an eluent to give the desired product (25) (399 mg, 79.2% yield); $^1$H-NMR (CDCl$_3$, 400 MHz) δ: 7.45 (m, 1H), 6.73 (d, J=8.0 Hz, 1H), 6.57 (d, J=8.0 Hz, 1H), 5.89 (m, 1H), 4.37 (m, 2H), 4.12 (m, 2H), 3.90 (m, 1H), 3.61 (m, 2H), 3.51 (s, 3H), 3.05–2.75 (m, 3H), 2.06 (m, 4H), 1.80–1.95 (m, 3H), 1.63 (m, 1H), 1.45 (s, 9H), 1.44 (m, 1H), 1.33 (s, 3H), 1.23 (m, 1H), 0.98 (s, 9H), 0.70 (m, 1H). See FIG. 9.

Preparation of Compound (26)

To a solution of (25) (399 mg, 0.598 mmol) in MeOH (15 ml) and H$_2$O (1.5 ml) was added NaOH (470 mg, 11.75 mmol). The reaction was stirred at room temperature for 3 hours. Most of MeOH was removed by rotary evaporation and water (10 ml) was added. The aqueous phase was extracted with CH$_2$Cl$_2$ (3×50 ml). The combined organic phase was dried over Na$_2$SO$_4$. The organic phase was filtered and concentrated to dryness. The residue was purified by flash column chromatography (silica gel) using ethyl acetate/hexane (2/3) as an eluent to give compound (26) (248 mg, 73%); $^1$H-NMR (CDCl$_3$, 400 MHz) δ: 6.78 (d, J=8.0 Hz, 1H), 6.60 (d, J=8.0 Hz, 1H), 5.83 (m, 1H), 4.41 (m, 2H), 4.22 (m, 1H), 4.13 (m, 2H), 3.90 (m, 1H), 3.55 (s, 3H), 3.10–2.80 (m, 7H), 2.10 (m, 2H), 1.80–1.95 (m, 5H), 1.70 (m, 1H), 1.45 (s, 9H), 1.36 (s, 3H), 1.16 (m, 1H), 1.02 (s, 9H), 0.70 (m, 1H). See FIG. 9.

Preparation of Compound (27)

To a stirred solution of (26) (248 mg, 0.4345 mmol) in THF (10 ml) was added diisopropylethylamine (0.3 ml, 1.723 mmol) and 2-Mercapto[S-acetyl]acetic acid N-hydroxysuccinimide ester (150 mg, 0.6487 mmol). The reaction mixture was stirred at room temperature for 3 hours. TLC analysis of the mixture showed that a less polar spot as a product in comparison with 26. The organic solvent was removed to dryness by rotary evaporation under reduced pressure. The residue was purified by flash column chromatography (silica gel) using ethyl acetate/hexane (7/3) as the eluent to give the desired product (27) (260 mg, 87% yield). $^1$H-NMR (CDCl$_3$, 400 MHz) δ: 6.78 (d, J=8.0 Hz, 1H), 6.60 (d, J=8.0 Hz, 1H), 5.79 (m, 1H), 4.42 (m, 2H), 4.17–4.11 (m, 3H), 3.95 (m, 1H), 3.54 (s, 3H), 3.45 (m, 2H), 3.10–2.80 (m, 3H), 2.37 (s, 3H), 2.10 (m, 2H), 1.80–1.95 (m, 7H), 1.71 (m, 1H), 1.45 (s, 9H), 1.36 (s, 3H), 1.20 (m, 1H), 1.00 (s, 10H), 0.70 (m, 1H). See FIG. 9.

Preparation of Compound (28)

To a solution of (27) (258 mg, 0.3756 mmol) in CH$_2$Cl$_2$ (2 ml) was added TFA (0.4 ml). The reaction mixture was stirred at room temperature for 1 hour. TLC analysis of the reaction showed that starting material (27) disappeared and a new more polar spot displayed (silica gel, ethyl acetate/hexane=1/1). Most of CH$_2$Cl$_2$ and TFA were removed by rotary evaporation under reduced pressure. The residue was further dried under high vacuum to remove a trace of TFA for 24 hours. This gave the desired product (28); $^1$H-NMR (CDCl$_3$, 400 MHz) δ: 9.20 (m, 1H), 8.65 (m, 1H), 6.85 (d, J=8.0 Hz, 1H), 6.69 (d, J=8.0 Hz, 1H), 4.52 (m, 1H), 4.17 (m, 2H), 3.73 (m, 1H), 3.58 (s, 3H), 3.45 (m, 2H), 3.33 (m, 1H), 3.21–3.10 (m, 2H), 3.00 (m, 1H), 2.61 (m, 1H), 2.39 (s, 3H), 2.22 (m, 2H), 1.95–1.80 (m, 5H), 1.65 (m, 1H), 1.39 (s, 3H), 1.11–1.27 (m, 4H), 1.03 (s, 9H), 0.80 (m, 1H). See FIG. 9.

Preparation of Norbuprenorphine-SH-KLH Immunogen (33)

a) Preparation of Bromoacetyl KLH (32)

To a solution of KLH (200 mg) in NaH$_2$PO$_4$—Na$_2$HPO$_4$ buffer (pH=8.0, 0.1M, 50 ml) at 4° C. (ice-bath) was added a solution of bromoacetic acid NHS ester (58 mg, 0.244 mmol) in DMF (2.0 ml). The pH value was maintained at 8.0. The reaction mixture was stirred in the cold-room (4° C.) for 16 hours. The mixture was purified by a Sephadex G-25 column, eluting with NaH$_2$PO$_4$—Na$_2$HPO$_4$ buffer (pH=8.00, 0.1M). The eluted fractions from the column were monitored by UV at 280 nm. A clean separation between bromoacetyl-KLH and the hapten was obtained. Fractions containing the product were pooled together (150 ml) and concentrated to 50 ml of bromoacetyl-KLH (32) by an Amicon concentrator for the next reaction. See FIG. 10.

b) Preparation of Norbuprenorphine-SH-KLH Immunogen (33)

To a solution of (28) (221 mg, 0.315) in degassed (N$_2$) MeOH (5 mL) and H$_2$O (0.2 ml) was added K$_2$CO$_3$ (87 mg, 0.630 mmol) under nitrogen. The reaction mixture was stirred at room temperature under nitrogen for 1 hour. TLC analysis of the mixture showed that starting material (28) had disappeared and a new spot was formed as a product (silica gel, MeOH/CH$_2$Cl$_2$=1/9, I$_2$, Ellman's reagent). MeOH was filtered to remove excess K$_2$CO$_3$ and the filtrate was concentrated by rotary evaporation in room temperature. The residue was dried under high vacuum for 0.5 hour at room temperature to give the desired hapten (29). The activated hapten (29) was dissolved in DMF (0.8 ml) for the next reaction.

To a solution of bromoacetyl-KLH (32) (50 ml, pH=8.00) was added the above activated hapten (29) solution slowly at 4° C. under nitrogen. The pH value was maintained at 8.0. The reaction was stirred at 4° C. (cold room) for 16 hours. The reaction mixture was separated using a Sephadex G-25 column equilibrated with NaH$_2$PO$_4$—Na$_2$HPO$_4$ buffer (pH=7.0, 0.1 M). The UV detector at 280 nm monitored the eluted fractions from the column. A clean separation between KLH immunogen and the hapten was obtained. Fractions containing protein (33) were pooled to a total volume of 180 ml and concentrated to 105 ml. The concentration of immunogen (33) was measured by using BCA Protein Concentration Assay. The Immunogen (33) had a concentration of 0.96 mg/ml with a hapten number of 1280, and was used for the immunizations. See FIG. 10.

Preparation of Compound (35)

To a solution of norbuprenorphine hydrochloride (2) (100 mg, 0.222 mmol) in DMF (4 ml) was added Et$_3$N (0.27 ml, 1.94 mmol). The reaction was stirred at room temperature for 0.5 hour. A solution of succinic anhydride (53 mg, 0.53 mmol) in DMF (1 ml) was added into the mixture. The reaction was stirred at room temperature for 4 hours. Most of the DMF was removed by rotary evaporation under reduced pressure. Water (10 ml) was added and the aqueous phase was adjusted to a pH value of 2.0 with 1 N HCl. The aqueous phase was extracted with EtOAc (3×30 mL). The combined organic phase was washed with water (2×10 mL) and dried over MgSO$_4$. The organic phase was filtered and concentrated to dryness. The residue was purified by flash column chromatography (silica gel) using CH$_2$Cl$_2$/MeOH/AcOH (92/8/0.1) as an eluent to give compound (35). FAB-MS m/z: 514 (MH$^+$, 20), 496 (M$^+$—H$_2$O, 100); $^1$H-NMR (CDCl$_3$, 400 MHz) δ: 6.74 (d, J=8.03 Hz, 1H), 6.54 (d, J=8.10 Hz, 1H), 5.87 (m, 1H), 4.82 (d, J=6.9 Hz, 1H), 4.43 (m, 1H), 3.68 (m, 1H), 3.52 (s, 3H), 3.30 (m, 1H), 2.50–2.95 (m, 8H), 1.75–2.10 (m, 6H), 1.31 (s, 3H), 1.21 (m, 1H), 0.96 (m, 9H), 0.73 (m, 1H). See FIG. 11.

Preparation of Norbuprenorphine-N-BSA Immunogen (37)

To a solution of (35) (58 mg, 0.113 mmol) in THF (3.0 m) was added DCC (35 mg, 0.17 mmol) and NHS ester (30.0 mg, 0.26 mmol). The reaction was stirred at room temperature under argon for 16 hours. The precipitate from the reaction was filtered off and THF was removed by rotary evaporation. The activated hapten (36) was dissolved in DMF (0.8 ml) for the next reaction.

To a solution of BSA (40 mg, 10 ml, NaH$_2$PO$_4$—Na$_2$HPO$_4$ buffer, pH=8.00) was added the above activated hapten (36) solution slowly at 4° C. under nitrogen. The pH value was maintained at 8.0. The reaction was stirred at 4° C. (cold room) for 16 hours. The reaction mixture was separated using a Sephadex G-25 column equilibrated with NaH$_2$PO$_4$—Na$_2$HPO$_4$ buffer (pH=7.0, 0.1 M). The UV detector at 280 nm monitored the eluted fractions from the column. A clean separation between BSA immunogen and the hapten was obtained. Fractions containing protein (37) were pooled to a total volume of 180 ml and concentrated to 105 ml. The concentration of immunogen (37) was measured by using BCA Protein Concentration Assay. The immunogen (37) had a concentration of 1.0 mg/ml with a hapten number of 33, and was used for the immunizations. See FIG. 11.

Conjugation of 3K Mutant G6PDH with Haptens Containing Bromoacetamido- or Maleimido-Functional Groups, Like Hapten (13)

3K G6PDH mutant was buffer exchanged with 50 mM phosphate-1.0 mM EDTA, pH 7.25. A solution of the protein (2 mL at 5 mg/mL) was then mixed with a solution of dithioerythreitol (20 μL of a 0.5 M solution in the phosphate-EDTA buffer) and mixture incubated at 4° C. for 16 hours. The protein solution was then buffer exchanged with 50 mM phosphate-1.0 mM EDTA-0.025 mM DTT, pH 7.25. Thiol content of the protein, as determined by titration with a solution of dithiodipyridine, was found to be 1.5 thiols per mole of the protein. The protein solution (2 mL at 5 mg/mL) was mixed with 40 fold molar excess of a DMF solution (0.05 mL) of hapten (13) and reaction mixture stirred gently at 4° C. for 16–24 hours. Excess hapten (13) was separated from the enzyme-hapten conjugate by passing the reaction mixture over a column of Sephadex G 50 in 50 mM phosphate, pH 7.0. The column fractions containing the enzyme-hapten conjugate were pooled by measuring absorption at 280 nm.

Haptens (3), (4), (5), (18), and (22) were conjugated with G6PDH or a label protein including alkaline phosphatase, B-galactosidase and horse radish peroxidase using a conjugation procedure similar to that described above.

Coupling Native G6PDH with Haptens Containing Reactive Sulfhydril Groups, Like Hapten (29)

Native G6PDH was buffer exchanged with 50 mM phosphate-1.0 mM EDTA, pH 8.0. The protein solution (3.4 mL at 10 mg/mL) was mixed with a solution of Reactive Red 120 (0.6 mL at 30 mg/mL) in the phosphate buffer. The protein solution was cooled in an ice bath and mixed with aliquots (30 µL) of a 0.2 M solution of N-hydroxysucinimidyl bromoacetate in DMF. After incubation in ice bath for 1 hr enzyme activity was measured. This addition of the DMF aliquots was continued till the enzyme activity was found to be 90±2% as compared to that of the native enzyme. The reaction mixture was then combined with 0.45 mL of a 4.0 M solution of sodium bromide in water. The protein solution was then passed through a column of DEAE-Sephadex A25 (1×30 cm) pre-equilibrated and eluted with 0.1 M phosphate-0.4 M sodium bromide, pH 8.0. The protein solution was then buffer exchanged with 0.1 M phosphate-5.0 mM EDTA, pH 7.60 to remove excess salt. The derivatized protein was found to contain 0.97 moles of bromoacetamido groups per mole of the protein. The protein solution was mixed 40 fold molar excess of the thiol derivative of the hapten (29) in DMF (50 µL) and mixture stirred gently in a cold box for 16–24 hours. Excess hapten (29) was separated from the enzyme-hapten conjugate by passing the reaction mixture over a column of Sephadex G 50 in 50 mM phosphate, pH 7.0. The column fractions containing the enzyme-hapten conjugate were pooled by measuring absorption at 280 nm.

Assay using Reagents in Accordance with Embodiments of the Present Invention

The BUP antibodies and enzyme conjugates in accordance with the invention may be employed in assays for the detection of the respective analytes. Either of the immunogens (6), (10), or (11), (33) or (37) is injected into a mouse, rabbit or sheep to raise antibody. As mentioned previously, antibodies may be screened by known methods, and evaluating properties such as specificity, conjugate inhibition, curve size and cross-reactivity. The obtained antibody is spiked into the antibody diluent to prepare the antibody reagent. The antibody reagent consists of antibody as prepared above, buffer, stabilizers, preservatives, and the substrates for the enzyme conjugate NAD and glucose 6 phosphate. Enzyme conjugate comprising compound (5), (13) or (18) or (22) or (29) and G6PDH ort a label protein including alkaline phosphatase, B-galactosidase and horse radish peroxidase is spiked into the conjugate reagent to prepare the enzyme conjugate reagent. The enzyme conjugate reagent consists of the conjugate, buffer, stabilizers and preservatives.

The BUP and/or norBP antibodies and enzyme conjugates may be advantageously used in a homogeneous assay format to detect BUP in urine samples. An analyzer (instrument) useful to set up the assay is Syva 30-R Biochemical Analyzer (Syva Company, Cupertino Calif.). BUP containing urine sample is incubated with antibody reagent followed by the addition of the enzyme conjugate reagent. The enzyme conjugate activity decreases upon binding to the antibody. The enzyme conjugate, which is not bound to the antibody, catalyzes the oxidation of glucose 6-phosphate (G6P). The oxidation of G6P is coupled with the reduction of NAD$^+$ to NADH, which can be measured at 340 nm. The change in the absorbance at 340 nm can be measured spectrophotometrically. The BUP concentration in a urine specimen can be measured in terms of G6PDH activity. The increase in the rate at 340 nm is due to the formation of NADH and is proportional to the enzyme conjugate activity. An assay curve is generated using BUP spiked into negative urine. The assay rate increases with increasing the concentration of free drug in the sample.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A compound of the formula 4:

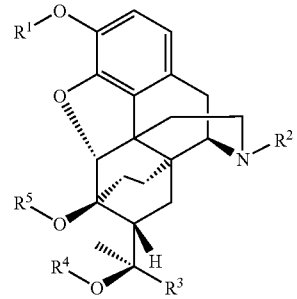

Formula 4 wherein $R^1$ is hydrogen; or protecting group, or glucuronide;

$R^2$ is a cyclopropyl methyl group, hydrogen or a protecting group;

$R^3$ is a t-butyl group;

$R^4$ is —Y-Z, and Y is a linking group and Z is selected from the group consisting of hydrogen, —OH, —SH, —S-acyl; —O-lower alkyl, halogen, NH2, -epoxy, -maleimidyl, haloacetamide, carboxyl, activated carboxyl, an immunogenic carrier, a protein or a label;

$R^5$ is a methyl group.

2. The compound of claim 1 wherein the linking group comprises 1–15 carbon atoms and/or 0–6 heteroatoms.

3. The compound of claim 1 wherein the linking group is selected from the group consisting of —(CH$_2$)n-C(O)—, or —C(O)(CH$_2$)n- or —C(O)(CH$_2$)n-NHC(O)—, or —C(O)(CH$_2$)n-NHC(O)(CH$_2$)n-, or —(CH$_2$)nSCH$_2$C(O)—, or —(CH$_2$)n-C(O)NH—(CH$_2$)n-, or —(CH$_2$)n-NH—C(O)—, or —(CH$_2$)n-NH—C(O)—(CH$_2$)n-, or —C(O)—(CH$_2$)n-; and n is an integer from 1 to 10, and including acid salts thereof.

4. The compound of claim 1 wherein the immunogenic carrier is BSA or KLH or selected from the group consisting of hemocyanins, globulins, albumines, and polysaccharides.

5. The compound of claim 1 wherein the protein is G6PDH or a label protein including alkaline phosphatase, B-galactosidase and horse radish peroxidase.

6. A compound of the formula 5:

Formula 5 wherein $R^1$ is hydrogen; or protecting group, or glucuronide;
$R^2$ is cyclopropyl methyl group, hydrogen or protecting group;
$R^3$ is a t-butyl group;
$R^4$ is a methyl group; and,
$R^5$ is —Y-Z, and Y is a linking group and Z is selected from the group consisting of hydrogen, —OH, —SH, —S-acyl; —O-lower alkyl, halogen, NH2, -epoxy, -maleimidyl, haloacetamide, carboxyl, activated carboxyl, an immunogenic carrier, a protein or a label.

7. The compound of claim 6 wherein the linking group comprises 1–15 carbon atoms and/or 0–6 heteroatoms.

8. The compound of claim 6 wherein the linking group is selected from the group consisting of —(CH$_2$)n-C(O)—, or —C(O)(CH$_2$)n- or —C(O)(CH$_2$)n-NHC(O)—, or —C(O)(CH$_2$)n-NHC(O)(CH$_2$)n-, or —(CH$_2$)nSCH$_2$C(O)—, or —(CH$_2$)n-C(O)NH—(CH$_2$)n-, or —(CH$_2$)n-NH—C(O)—, or —(CH$_2$)n-NH—C(O)—(CH$_2$)n-, or —C(O)—(CH$_2$)n-; n is an integer from 1 to 10, and including acid salts thereof.

9. The compound of claim 6 wherein the immunogenic carrier is BSA or KLH or selected from the group consisting of hemocyanins, globulins, albumines, and a polysacoharides.

10. The compound of claim 6 wherein the protein is G6PDH or a label protein including alkaline phosphatase, B-galactosidase and horse radish peroxidase.

11. A method for determining an amount of at least one of buprenorphine (BUP) or norbuprenorphine in a medium, said method comprising:
providing in combination in the medium:
a sample suspected of containing said at least one of buprenorphine (BUP) or norbuprenorphine; and,
an antibody raised against a compound of the formula of claim 1;
examining said medium for the presence of a complex comprising said at least one of buprenorphine (BUP) or norbuprenorphine and said antibody, the presence thereof indicating the presence of said at least one of buprenorphine (BUP) or norbuprenorphine in said sample.

12. A method according to claim 11 wherein the antibody is a monoclonal antibody.

13. A method for determining an amount of at least one of buprenorphine (BUP) or norbuprenorphine in a medium, said method comprising:
providing in combination in the medium:
a sample suspected of containing said at least one of buprenorphine (BUP) or norbuprenorphine; and,
an antibody raised against a compound of the formula of claim 6;
examining said medium for the presence of a complex comprising said at least one of buprenorphine (BUP) or norbuprenorphine and said antibody, the presence thereof indicating the presence of said at least one of buprenorphine (BUP) or norbuprenorphine in said sample.

14. A method according to claim 13 further wherein the antibody is a monoclonal antibody.

15. A method according to claim 11 wherein said combination further comprises a label conjugate of the formula of claim 1.

16. A method according to claim 13 wherein said combination further comprises a label conjugate of the formula of claim 6.

17. A kit for determining an amount of at least one of buprenorphine (BUP) or norbuprenorphine in a medium, said kit comprising:
an antibody raised against a compound of the formula of claim 1; and,
ancillary reagents for determining said at least one of buprenorphine (BUP) or norbuprenorphine compound.

18. A kit according to claim 17 wherein the antibody is a monoclonal antibody.

19. A kit for determining an amount of at least one of buprenorphine (BUP) or norbuprenorphine in a medium, said kit comprising:
an antibody raised against a compound of the formula of claim 6; and,
ancillary reagents for determining said at least one of buprenorphine (BUP) or norbuprenorphine compound.

20. A kit according to claim 19 wherein the antibody is a monoclonal antibody.

21. The kit of claim 17 further comprising a label conjugate of the formula of claim 1.

22. The kit of claim 19 further comprising a label conjugate of the formula of claim 6.

23. The compound of claim 1 wherein the activated carboxy group is selected from the group consisting of hydroxysuccinimidyl,-succinimidyi,-carbonate, anhydride and imidate.

24. The compound of claim 6 wherein the activated carboxy group is selected from the group consisting of hydroxysuccinimidyl,-succinimidyl,-carbonate, anhydride and imidate.

25. The method of claim 11 wherein the antibody further specifically binds metabolites selected from the group consisting of glucuronide metabolites of norbuprenorphine and glucuronide metabolites of buprenorphine.

26. The method of claim 13 wherein the antibody further specifically binds metabolites selected from the group consisting of glucuronide metabolites of norbuprenorphine and glucuronide metabolites of buprenorphine.

27. The kit of claim 17 wherein the kit is further used for determining an amount of metabolites selected from the group consisting of glucuronide metabolites of norbuprenorphine and glucuronide metabolites of buprenorphine.

28. The kit of claim 19 wherein the kit is further used for determining an amount of metabolites selected from the group consisting of glucuronide metabolites of norbuprenorphine and glucuronide metabolites of buprenorphine.

* * * * *

UNITED STATES PATENT AND TRADEMARK OFFICE
CERTIFICATE OF CORRECTION

PATENT NO.        : 7,220,842 B2
APPLICATION NO. : 10/818115
DATED             : May 22, 2007
INVENTOR(S)       : Zheng et al.

It is certified that error appears in the above-identified patent and that said Letters Patent is hereby corrected as shown below:

In Claim 9, Col. 25, line 40, please delete "polysacoharides" and insert
-- polysaccharides --

In Claim 23, Col. 26, line 43, please delete "-succinimidyi," and insert
-- -succinimidyl,--

Signed and Sealed this

Eighteenth Day of March, 2008

JON W. DUDAS
*Director of the United States Patent and Trademark Office*